United States Patent
Woods et al.

(10) Patent No.: US 10,932,748 B2
(45) Date of Patent: Mar. 2, 2021

(54) SIX DEGREES-OF-FREEDOM QUALITY ASSURANCE PHANTOM FOR RADIATION THERAPY LINEAR ACCELERATORS

(71) Applicant: Ohio State Innovation Foundation, Columbus, OH (US)

(72) Inventors: Kyle Woods, Columbus, OH (US); Ahmet Ayan, Dublin, OH (US); Jeffrey Woollard, Hilliard, OH (US); Nilendu Gupta, Westerville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/639,861

(22) PCT Filed: Aug. 17, 2018

(86) PCT No.: PCT/IB2018/056247
§ 371 (c)(1),
(2) Date: Feb. 18, 2020

(87) PCT Pub. No.: WO2019/035093
PCT Pub. Date: Feb. 21, 2019

(65) Prior Publication Data
US 2020/0359988 A1   Nov. 19, 2020

Related U.S. Application Data

(60) Provisional application No. 62/547,597, filed on Aug. 18, 2017.

(51) Int. Cl.
*G01D 18/00* (2006.01)
*A61N 5/10* (2006.01)
(Continued)

(52) U.S. Cl.
CPC ............ *A61B 6/583* (2013.01); *A61B 6/032* (2013.01); *A61B 6/0407* (2013.01); *A61B 6/08* (2013.01);
(Continued)

(58) Field of Classification Search
CPC .. C12Q 1/6883; G01N 33/5011; G01N 33/68; A61N 5/1049; A61N 2005/1058;
(Continued)

(56) References Cited

U.S. PATENT DOCUMENTS

| 5,553,112 A | * | 9/1996 | Hardy | ...................... A61B 6/08 378/206 |
| 6,626,569 B2 | * | 9/2003 | Reinstein | ............. A61N 5/1048 250/252.1 |

(Continued)

OTHER PUBLICATIONS

International Search Report and Written Opinion issued by the International Searching Authority (ISA/US) in PCT Application No. PCT/IB2018/056247 dated Nov. 26, 2018. 7 pages.

(Continued)

*Primary Examiner* — Irakli Kiknadze
(74) *Attorney, Agent, or Firm* — Meunier Carlin & Curfman LLC

(57) ABSTRACT

A three-dimensional phantom for providing displacement profiles for a CT table having 6 degrees of freedom includes a body having at a top face, a side face and an end face; the top face and the side face sharing a common edge; the top face and the end face sharing a common edge; and the side face and the end face sharing a common edge; wherein an angle formed by the top face and the end face is less than 90 degrees; the side face including a first isocenter mark and a first offset mark, wherein the first offset mark has an angle (Continued)

corresponding to the angle formed by the top face and the end face; and an isocenter marker at the isocenter of the body.

18 Claims, 35 Drawing Sheets

(51) Int. Cl.
```
A61B 6/00      (2006.01)
A61B 6/04      (2006.01)
A61B 6/08      (2006.01)
A61B 6/03      (2006.01)
```
(52) U.S. Cl.
CPC .... *A61N 5/1075* (2013.01); *A61N 2005/1076* (2013.01)

(58) Field of Classification Search
CPC .... A61N 2005/1055; A61N 2005/1063; A61N 5/1042; A61N 5/1079; A61N 5/1048; A61N 5/1075; A61N 2005/1052; A61N 2005/1061; A61N 5/1071; A61N 5/103; A61N 2005/1091; A61N 5/1017; A61N 5/1037; A61N 5/1064; A61N 2005/1074; A61N 5/1067; A61N 2005/1051; A61N 2005/1057; A61N 5/107; A61N 2005/105; A61N 2005/1059; A61N 2005/1076; A61N 2005/1072; G01R 33/4808; G01R 33/4812; G01R 33/58; A61B 6/583; A61B 6/584; A61B 2560/0228; A61B 6/0492; A61B 6/08; A61B 6/547; A61B 6/582; A61B 2034/2055; A61B 2034/2063; A61B 2034/2065; A61B 2090/378; A61B 34/20; G01T 1/169; G06T 2207/10132; A61F 2009/00844; A61F 2009/00863; A61F 9/008
USPC ...................................... 378/18, 65, 205–209
See application file for complete search history.

(56) References Cited

U.S. PATENT DOCUMENTS

| | | | | |
|---|---|---|---|---|
| 7,729,472 | B2 * | 6/2010 | Scherch | A61B 6/0492 378/65 |
| 10,069,519 | B1 * | 9/2018 | Millar | H03M 13/3911 |
| 2005/0013406 | A1 * | 1/2005 | Dyk | A61N 5/1049 378/65 |
| 2010/0237257 | A1 | 9/2010 | Saracen et al. | |
| 2011/0150186 | A1 | 6/2011 | Ziegler et al. | |
| 2015/0085993 | A1 * | 3/2015 | Scheib | A61N 5/1049 378/207 |

OTHER PUBLICATIONS

Woods, K., et al. "SU-E-T-234: Daily Quality Assurance for a Six Degrees of Freedom Couch Using a Novel Phantom." Medical physics 42.6 Part15 (2015): 3386-3386.

Avelino SR, Silva LF, Miosso CJ. Use of 3D-printers to create intensity-modulated radiotherapy compensator blocks. Conf Proc IEEE Eng Med Biol Soc. 2012;2012:5718-5721.

Ayan AS, Lin H, Yeager C, et al. Should image rotation be addressed during routine cone-beam CT quality assurance? Phys Med Biol. 2013;58(4):1059-1073.

Bieniosek MF, Lee BJ, Levin CS. Technical Note: Characterization of custom 3D printed multimodality imaging phantoms. Med Phys. 2015;42(10):5913-5918.

Brandmeir NJ, McInerney J, Zacharia BE. The use of custom 3D printed stereotactic frames for laser interstitial thermal ablation: technical note. Neurosurg Focus. 2016;41(4):E3.

Canters RA, Lips IM, Wendling M, et al. Clinical implementation of 3D printing in the construction of patient specific bolus for electron beam radiotherapy for non-melanoma skin cancer. Radiother Oncol. 2016;121(1):148-153.

Chiesa S, Placidi L, Azario L, et al. Adaptive optimization by 6 DOF robotic couch in prostate volumetric IMRT treatment: rototranslational shift and dosimetric consequences. J Appl Clin Med Phys. 2015;16(5):5525.

Cunha JA, Mellis K, Sethi R, et al. Evaluation of PC-ISO for customized, 3D Printed, gynecologic 192-Ir HDR brachytherapy applicators. J Appl Clin Med Phys. 2015;16(1).

Dhabaan A, Schreibmann E, Siddiqi A, et al. Six degrees of freedom CBCT-based positioning for intracranial targets treated with frameless stereotactic adiosurgery. J Appl Clin Med Phys. 2012;13(6):3916.

Dodziuk H. Applications of 3D printing in healthcare. Kardiochir Torakochirurgia Pol. 2016;13(3):283-293.

Du W, Yang JN, Chang EL, et al. A quality assurance procedure to evaluate cone-beam CT image center congruence with the radiation isocenter of a linear accelerator. J Appl Clin Med Phys. 2010;11(4):3297.

Ehler ED, Barney BM, Higgins PD, Dusenbery KE. Patient specific 3D printed phantom for IMRT quality assurance. Phys Med Biol. 2014;59(19):5763-5773.

Gevaert T, Verellen D, Engels B, et al. Clinical evaluation of a robotic 6-degree of freedom treatment couch for frameless radiosurgery. Int J Radiat Oncol Biol Phys. 2012;83(1):467-474.

Guckenberger M, Meyer J, Wilbert J, Baier K, Sauer O, Flentje M. Precision of image-guided radiotherapy (IGRT) in six degrees of freedom and limitations in clinical practice. Strahlenther Onkol. 2007;183(6):307-313.

Huang CY, Tehrani JN, Ng JA, Booth J, Keall P. Six degrees-of-freedom prostate and lung tumor motion measurements using kilovoltage intrafraction monitoring. Int J Radiat Oncol Biol Phys. 2015;91(2):368-375.

Jin JY, Yin FF, Tenn SE, Medin PM, Solberg TD. Use of the BrainLAB ExacTrac X-Ray 6D system in image-guided radiotherapy. Med Dosim. 2008;33(2):124-134.

Jung JW, Lee JS, Cho DW. Computer-aided multiple-head 3D printing system for printing of heterogeneous organ/tissue constructs. Sci Rep. 2016;6:21685.

Klein EE, Hanley J, Bayouth J, et al. Task Group 142 report: quality assurance of medical accelerators. Med Phys. 2009;36(9):4197-4212.

Lee MY, Han B, Jenkins C, Xing L, Suh TS. A depth-sensing technique on 3D-printed compensator for total body irradiation patient measurement and treatment planning. Med Phys. 2016;43(11):6137.

Lutz W, Winston KR, Maleki N. A system for stereotactic radiosurgery with a linear accelerator. Int J Radiat Oncol Biol Phys. 1988;14(2):373-381.

Madamesila J, McGeachy P, Villarreal Barajas JE, Khan R. Characterizing 3D printing in the fabrication of variable density phantoms for quality assurance of radiotherapy. Phys Med. 2016;32(1):242-247.

Michiels S, D'Hollander A, Lammens N, et al. Towards 3D printed multifunctional immobilization for proton therapy: Initial materials characterization. Med Phys. 2016;43(10):5392.

Park K, Park S, Jeon MJ, et al. Clinical application of 3D-printed-step-bolus in post-total mastectomy electron conformal therapy. Oncotarget. 2016.

Ricotti R, Vavassori A, Bazani A, et al. 3D-printed applicators for high dose rate brachytherapy: Dosimetric assessment at different infill percentage. Phys Med. 2016;32(12):1698-1706.

Ripley B, Levin D, Kelil T, et al. 3D printing from MRI Data: Harnessing strengths and minimizing weaknesses. J Magn Reson Imaging. 2017;45(3):635-645.

Schmidhalter D, Fix MK, Wyss M, et al. Evaluation of a new six degrees of freedom couch for radiation therapy. Med Phys. 2013;40(11):111710.

(56) References Cited

OTHER PUBLICATIONS

Schmidhalter D, Malthaner M, Born EJ, et al. Assessment of patient setup errors in IGRT in combination with a six degrees of freedom couch. Z Med Phys. 2014;24(2):112-122.

Shi C, Tazi A, Fang DX, Iannuzzi C. Study of ExacTrac X-ray 6D IGRT setup uncertainty for marker-based prostate IMRT treatment. J Appl Clin Med Phys. 2012;13(3):3757.

Su S, Moran K, Robar JL. Design and production of 3D printed bolus for electron radiation therapy. J Appl Clin Med Phys. 2014;15(4):4831.

Tack P, Victor J, Gemmel P, Annemans L. 3D-printing techniques in a medical setting: a systematic literature review. Biomed Eng Online. 2016;15(1):115.

Takakura T, Mizowaki T, Nakata M, et al. The geometric accuracy of frameless stereotactic radiosurgery using a 6D robotic couch system. Phys Med Biol. 2010; 55(1):1-10.

Takemura A, Ueda, S., Noto, K., Kojima, H., Isomura, N. Comparison of the motion accuracy of a six degrees of freedom radiotherapy couch with and without weights. International Journal of Medical Physics, Clinical Engineering and Radiation Oncology. 2013;2:69-75.

Ventola CL. Medical Applications for 3D Printing: Current and Projected Uses. P T. 2014;39(10):704-711.

Xing L, Thorndyke B, Schreibmann E, et al. Overview of image-guided radiation therapy. Med Dosim. 2006;31(2):91-112.

International Preliminary Report on Patentability issued for Application No. PCT/IB2018/056247, dated Feb. 27, 2020.

* cited by examiner

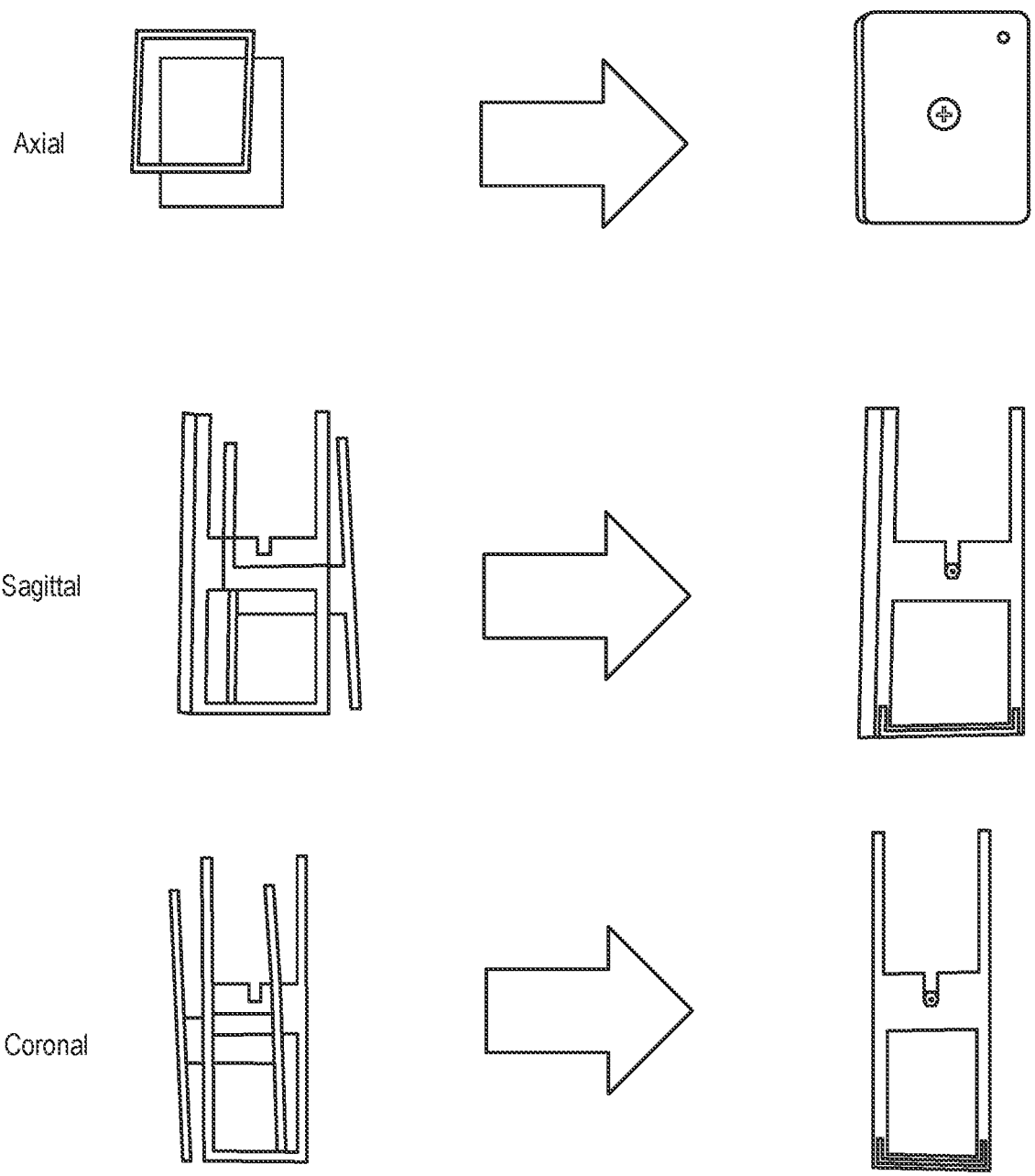

SIX DEGREES-OF-FREEDOM QUALITY ASSURANCE PHANTOM FOR RADIATION THERAPY LINEAR ACCELERATORS

CROSS-REFERENCE TO RELATED APPLICATIONS

This application is a national stage application filed under 35 U.S.C. § 371 of PCT/IB2018/056247 filed Aug. 17, 2018, which claims the benefit of U.S. Provisional Patent Application Ser. No. 62/547,597 filed Aug. 18, 2017, which is expressly incorporated herein by reference.

BACKGROUND

Field of the Invention

Embodiments of the present invention relate to phantom for aligning a linear accelerator for application of radiation therapy, specifically a phantom for use in conjunction with 6-degree of freedom (6DoF) treatment tables.

Background

Radiation therapy devices for the treatment of tumors in patients, using radiation emitting devices, are well known. A radiation therapy device generally includes a gantry which can be swiveled around a horizontal axis of rotation in the course of a therapeutic treatment. A linear accelerator (LINAC) is located within the gantry for generating a high energy radiation beam for therapy. This high energy radiation beam may be an electron beam or photon (x-ray) beam, for example. During treatment, the radiation beam is focused within a target of a patient lying in the isocenter of the gantry rotation.

The alignment of the radiotherapy simulators and treatment machines must be checked regularly to maintain accurate localization and delivery. Comprehensive quality assurance tools are used in order to maintain a high degree of treatment delivery accuracy to any planned treatments, so that the absolute dose delivered is consistent with the planned or prescribed dose. In radiation therapy, it is important to ensure that the absolute dose delivered is consistent with the planned dose, and that the critical spatial resolution of that dose is consistent with the planned dose distribution.

The robotic patient positioning table is a vital component in external beam radiation therapy treatments. These tables can mechanically drive a patient to a desired treatment position with the aid of external skin marks or fiducials. Furthermore, most modern LINACs are equipped with two- or three-dimensional image guidance in order to correct for and minimize interfractional setup uncertainties. Image-guided radiation therapy (IGRT) has improved accuracy for daily treatments and have allowed clinicians to decrease planning target volumes in order to spare normal tissues. However, with LINAC-based treatments demanding greater accuracy, quality assurance (QA) tolerances for image-guidance and table positioning must be in congruence with more precise treatments. The American Association in Physicists in Medicine (AAPM) task group report 142 (TG-142) regarding quality assurance on medical accelerators specifies these tolerances with the type of treatment being delivered, especially with more complex modalities like intensity modulated radiation therapy (IMRT), stereotactic radiotherapy (SRT) and stereotactic body radiation therapy (SBRT)

Conventional treatment tables are designed with four degrees-of-freedom (4DoF) in order to adjust positioning in the patient's vertical, lateral, and longitudinal directions, as well as an additional yaw rotation. A relatively new technology that is being outfitted on LINACs are robotic six degrees-of freedom (6DoF) tables that allow for mechanical adjustments of pitch and roll rotations in addition to the standard 4DoF adjustments.

Clinical indications of on-line rotational adjustments have also been investigated. A theoretical study of rotational corrections by Ayan et al. showed that depending on the shape of the target volume, the effect of not-correcting rotational mismatches could be very detrimental dosimetrically. Both Gavaert et al. and Dhabaan et al. noted improved dosimetric quantities for intracranial stereotactic patients when using 6DoF corrections compared to 4DoF. 6DoF analysis of prostate treatments showed more variability. Chiesa et al. noted minimal dosimetric impact for spherical prostate targets with 6DoF corrections but potentially significant dosimetric deviations for elongated targets with seminal vesicle involvement. Other prostate studies observed rotational adjustments greater than 2° and commented on the importance to correct for larger deviations. Two studies categorized 6DoF accuracy in terms generalized disease sites. Guckennberger et al. compared 6DoF set accuracies in terms of non-fixated immobilization (body) and fixated immobilization (cranial or head and neck). Schmidhalter et al. classified 6DoF accuracies by cranial and extracranial treatments. In both studies, it was observed that extracranial, or body-type, treatments required a larger translational and rotational correction.

While clinical implementation of 6DoF tables yields more accurate image-guided results, routine quality assurance (QA) for 6DoF tables has been limited. Schmidhalter et al has demonstrated reproducible 6DoF table performance using a combination of graph paper, inclinometers, and imaging methods. These tests have demonstrated a process in which routine QA for 6DoF tables can be established. While 6DoF commissioning and QA have been characterized by other studies, it is to the best of our knowledge that a streamlined procedure has yet to be developed.

There are several commercial phantoms capable of simultaneously testing some of the above requirements (WLQA by Sun Nuclear [Melbourne, Fla.], ISO Cube Model 023 by CIRS [Norfolk, Va.], MIMI Phantom by Standard Imaging [Middleton, Wis.]). However, these phantoms either need an adapter to test for 6DoF corrections (originally designed for 4DoF) or they are not capable of including additional routine QA. Literature review shows several authors specifically testing 6DoF tables. Schmidhalter et al. has demonstrated 6DoF QA table performance using a combination of graph paper, inclinometers, and imaging methods [Schmidhalter D, et al. Evaluation of a new six degrees of freedom couch for radiation therapy. Med Phys. 2013]. However, these tests are rudimentary and take significant amount of time to perform. Other authors used anthropomorphic phantoms in order to characterize 6DoF tables [Jin J Y, et al. Use of the BrainLAB ExacTrac X-Ray 6D system in image-guided radiotherapy. Med Dosim.; Takakura T, et al. The geometric accuracy of frameless stereotactic radiosurgery using a 6D robotic couch system. Phys Med Biol.]. These methods are too cumbersome to establish QA on a daily basis.

BRIEF SUMMARY

Accordingly, the present disclosure is directed to a six degrees-of-freedom quality assurance phantom for radiation therapy linear accelerators that obviates one or more of the problems due to limitations and disadvantages of the related art.

In accordance with the purpose(s) of this invention, as embodied and broadly described herein, this invention, in one aspect, relates to a three-dimensional phantom for aligning a linear accelerator for radiation therapy equipped with a six degrees-of-freedom (6DoF) treatment table, comprising: a body having at a top face, a side face and an end face; the top face and the side face sharing a common edge; the top face and the end face sharing a common edge; and the side face and the end face sharing a common edge; wherein an angle formed by the top face and the end face is less than 90 degrees; the side face including a first isocenter mark and a first offset mark, wherein the first offset mark has an angle corresponding to the angle formed by the top face and the end face; and an isocenter marker at the isocenter of the body.

In another aspect, the invention relates to a method of performing an alignment test for a computer tomography (CT) table having 6 degrees of freedom for use with a linear accelerator (LINAC) having alignment lasers, the method comprising placing a three-dimensional phantom on the CT table, the three-dimensional phantom having a body having at a top face, a side face and an end face; the top face and the side face sharing a common edge; the top face and the end face sharing a common edge; and the side face and the end face sharing a common edge; wherein an angle formed by the top face and the end face is less than 90 degrees; the side face including a first isocenter mark and a first offset mark, wherein the first offset mark has an angle corresponding to the angle formed by the top face and the end face; and an isocenter marker at the isocenter of the body; aligning the alignment lasers with the first offset mark; performing an cone-beam scan of the three-dimensional phantom to produce a data set; comparing the data set with an initial data set previously generated with respect to the phantom leveled to be a true rectangular prism to produce a displacement profile to correct for translations in at least one of the lateral, longitudinal and vertical directions, roll, pitch and yaw of the CT table; and applying the displacement profile to CT table; and verifying alignment of the CT table by checking alignment of the alignment lasers against the isocenter marks.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Further embodiments, features, and advantages of the six degrees-of-freedom quality assurance phantom for radiation therapy linear accelerators, as well as the structure and operation of the various embodiments of the six degrees-of-freedom quality assurance phantom for radiation therapy linear accelerators, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate a six degrees-of-freedom quality assurance phantom for radiation therapy linear accelerators. Together with the description, the figures further serve to explain the principles of the a six degrees-of-freedom quality assurance phantom for radiation therapy linear accelerators described herein and thereby enable a person skilled in the pertinent art to make and use the a six degrees-of-freedom quality assurance phantom for radiation therapy linear accelerators.

FIG. 13A-13B show the online match of the reference CT and CBCT, that is, an example of on-line CBCT with initial setup of phantom in axial, sagittal, and coronal views.

DETAILED DESCRIPTION OF THE INVENTION

Figure 1:
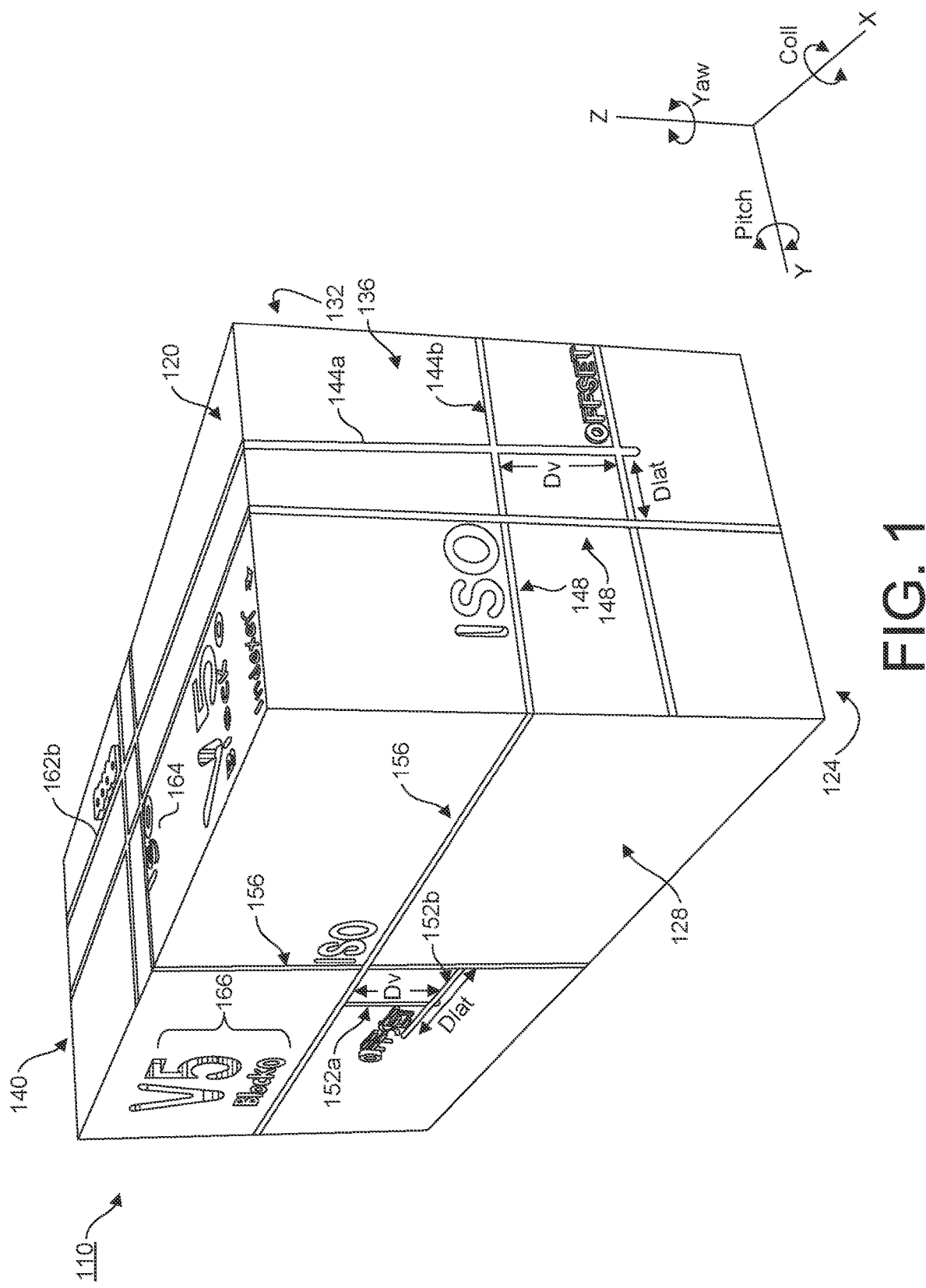
FIG. 1 illustrates an elevation view of a phantom according to principles of the present disclosure.

Reference will now be made in detail to embodiments of the a six degrees-of-freedom quality assurance phantom for radiation therapy linear accelerators with reference to the accompanying figures, in which like reference numerals indicate like elements.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

Throughout this application, various publications may have been referenced. The disclosures of these publications in their entireties are hereby incorporated by reference into this application in order to more fully describe the state of the art to which this invention pertains.

Accordingly, a quality assurance phantom has been developed that can be used to satisfy many regulated tests for six degrees-of-freedom (6DoF) treatment tables for linear accelerators (LINAC) in radiation oncology. 6DoF treatment tables allow for 2 additional degrees (pitch and roll) compared to traditional 4DoF (vertical, lateral, longitudinal, and yaw) when correcting for patient setup during image-guidance prior to treatment delivery. Since this 6DoF technology is relatively new, few quality assurance (QA) devices have been developed in order to test this new technology in a streamlined manner.

A phantom according to principles of the present disclosure was created using a computer aided design (CAD) software. A prototype was develop using a 3D printer, although manufacture of the phantom according to principles of the present disclosure is not limited to 3D printing, as described herein. The prototype was developed using fused deposition modeling (FDM) in what would be typically called a "hobby" or "desktop" printer. The design includes known angulation to the faces of the print in order to correct for skewness during QA testing. At the center of the phantom, a ball bearing (BB) was placed for isocentricity testing, which tests the coincidence between the mechanical and radiation isocenter (coordinate origin). With a straight reference image taken at simulation (using 3D printed leveler to straighten device), the phantom is volumetrically imaged at an offset position and angulation. During image registration, the phantom is corrected using an iterative registration algorithm that adjusts the phantom for rotation and translation based on the aligned reference image. This design not only can be used to test the new 6DoF technology, but it also consolidates several additional regulated LINAC daily tests, which include:

Table rotation and position
External laser alignment
Isocentricity of mechanical and radiation isocenter
Volumetric imaging registration According to principles of the present disclosure, a phantom for use in quality assurance testing of 6 degrees-of-freedom (6DoF) robotic tables is an imperfect rectangular prism, i.e., the six-sided structure is not comprised of all right angled sides and may be made of any plastic or material roughly equivalent to human or animal tissue. The variance from 90 degrees on any side or surface of the prism may be in a range of 0.5 degrees to 3 degrees, as discussed in more detail below.

FIG. 1 illustrates an elevation view of a phantom according to principles of the present disclosure. As illustrated, the phantom 110 is a three-dimensional structure having 6 faces: a top face 120, a bottom face (not seen) 124, a first side face 128 and a second side face 132, a first end face 136 and a second end face 140. By the nature of the elevation view, the bottom face, the second side face and the second end face are not seen in FIG. 1.

In the exemplary embodiment illustrated in FIG. 1, the top face 120 is a rectangle in which the two corners adjacent to second end face 140 are 90° angles. The corner at the intersection of the top face 120, the first side face 128, and the first end face 136 on the top face 120 forms greater than 90°, and the corner at the intersection of the top face 120, the second side face 132, and the first end face 136 on the top face 120 forms less than 90°. The side face 128 is an imperfect rectangle, in which the angle between the edges adjacent the first end face 136 and the second end face 140 and the edge adjacent the top face 120 are 90° angles and the angle between the edge adjacent the bottom face 124 and the edge adjacent the first end face 136 is less than 90° and the angle between the edge adjacent the bottom face 124 and the edge adjacent the second end face 140 is greater than 90°.

Figure 3:
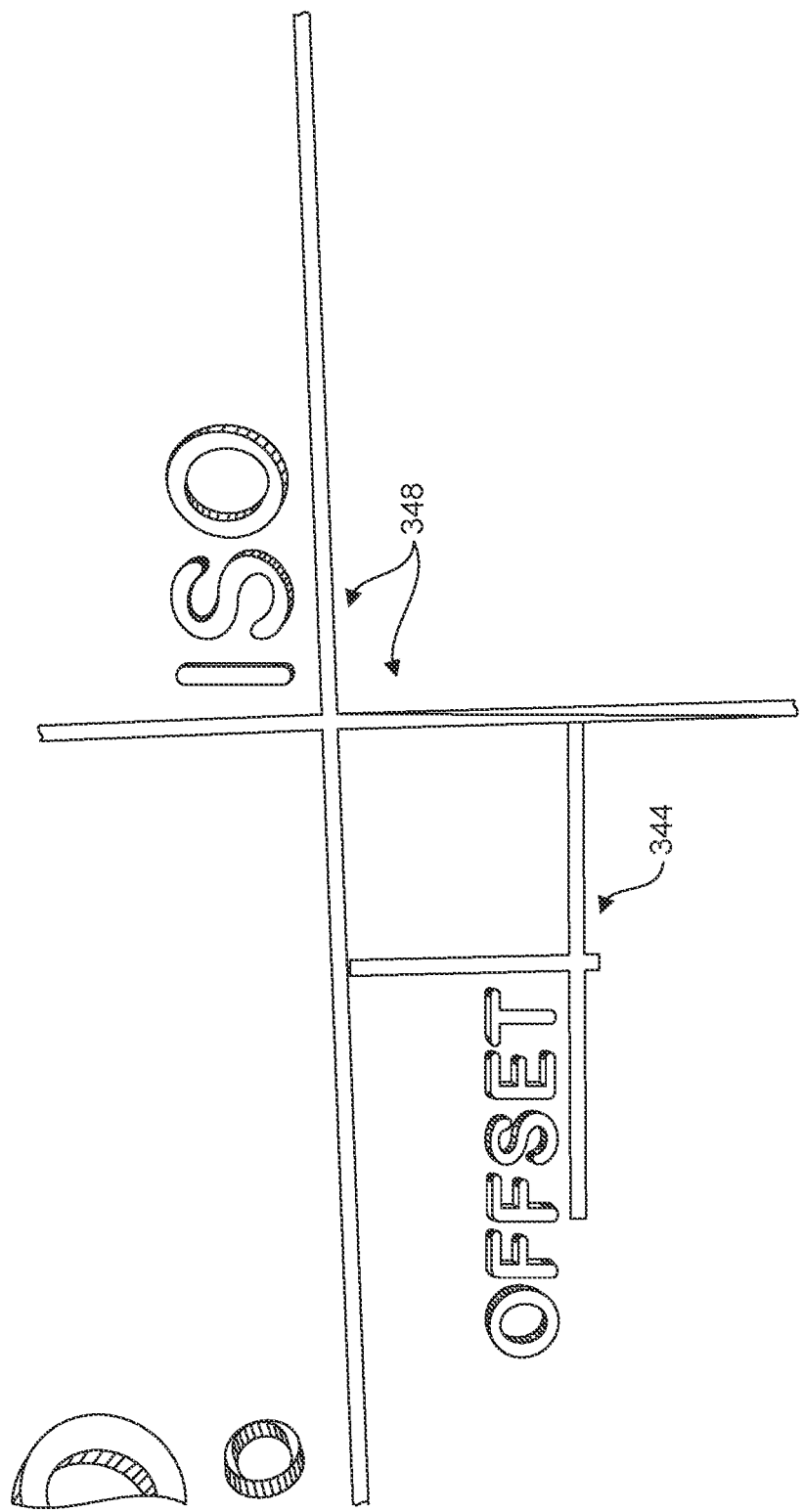
FIG. 3 illustrates an exploded view of exemplary isocenter lines of FIG. 1.

As illustrated in FIG. 1, the first end face 136 includes a set of end face offset marks 144a and 144b and a set of end face isocenter marks 148. The offset marks 144 include a roughly vertical line offset mark 144a and a roughly horizontal line offset mark 144b. The vertical line offset mark 144a is at a 2 degree offset from vertical and the horizontal line offset mark is at a 2 degree offset from horizontal. The degree variance from vertical for the vertical offset mark 144a may be in the range of 0.5 to 3 degrees. The degree variance from horizontal for the horizontal offset mark 144a may be in the range of 0.5 to 3 degrees. The isocenter marks 148 are substantially 90 degrees to each other and indicate the isometric center of the phantom at the end face 136. FIG. 3 illustrates an exploded view of exemplary isocenter lines 348 and offset marks 344 for a side face of the phantom. The offset marks are used for initial laser alignment, and the isocenter marks are used for final visual verification of 6DoF adjustments (with the field light and lasers.

As illustrated in FIG. 1, the first side face 128 includes a set of side face offset marks 152a and 152b and a set of side face isocenter marks 156. The side face offset marks 152a and 152b include a roughly vertical line offset mark 152a and a roughly horizontal line offset mark 152b. The vertical line offset mark 152a is at a 2 degree offset from vertical and the horizontal line offset mark 152b is at a 2 degree angle offset from horizontal. The degree variance from vertical for the vertical offset mark 152a may be in the range of 0.5 to 3 degrees. The degree variance from horizontal for the horizontal offset mark 152b may be in the range of 0.5 to 3 degrees. The isocenter marks 156 are substantially 90 degrees to each other and indicate the isometric center of the phantom at the first side face 128.

As illustrated in FIG. 1, the top face 120 includes a set of top face offset marks 162a and 162b and a set of top face isocenter marks 164. The top face offset marks 162a and 162b include a roughly vertical line offset mark 162a and a roughly horizontal line offset mark 162b. The vertical line offset mark 162a is at a 2 degree offset from vertical and the horizontal line offset mark 162b is at a 2 degree angle offset from horizontal. The degree variance from vertical for the vertical offset mark 162a may be in the range of 0.5 to 3 degrees. The degree variance from horizontal for the horizontal offset mark 162b may be in the range of 0.5 to 3 degrees. The isocenter marks 164 are substantially 90 degrees from each other and indicate an isometric center of the phantom at the top face 120.

Figure 4:
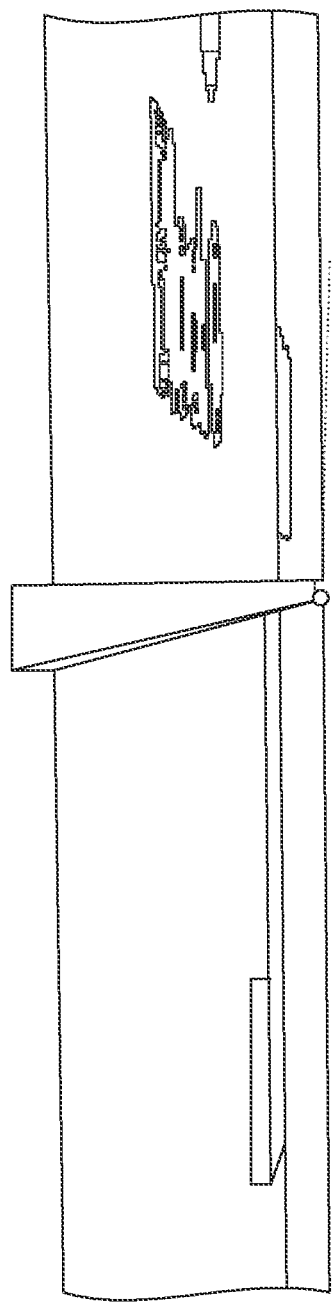
FIG. 4 illustrates exemplary depth of isocenter marks according to an aspect of the present disclosure.

The isocenter marks and the offset marks on any of the faces of the phantom may be visual marks only, i.e. have not depth or protrusion with respect to the phantom. The isocenter marks on each face may have a width of, for example 1 mm, to test tolerance of a visual laser system as part of the registration process, as illustrated in FIG. 4. The isocenter marks may have a width of, e.g., 1 to 2 mm, depending on the machine-type tolerance taken from the latest LINAC QA guidance documentation. While depth or protrusion with respect to the phantom is not required for either the isocenter marks or offset marks on any face of the phantom, the isocenter marks and the offset marks may be formed by creating indentions or protrusions with respect to the phantom during the manufacturing process rather than by or in addition to providing visual markings for the isocenter marks or the offset marks. In an aspect, the offset marks may protrude, while the isocenter mark are indented or vice versa to provide a three-dimensional reference in CT imaging, which may assist with registrations and alignment verification, although the primary purpose of both the offset and the isocenter marks is visual alignment during registration.

Intersection of the offset marks on the faces of the phantom indicate an offset from the isocenter in each direction in each direction (vertical, lateral, and longitudinal) by a known distance $D_v$, $D_{lat}$, $D_{long}$. The translational offset for the exemplary phantom is 1.50 cm in each direction (vertical, lateral, and longitudinal). This distances $D_v$, $D_{lat}$, $D_{long}$ can be modified just like the rotational offset, and can be equal to one another or can be the same. An offset larger than 1.50 cm may provide difficulties for the registration algorithm. Moreover, larger shifts may not necessarily be indicative of true patient scenario.

Figure 2:
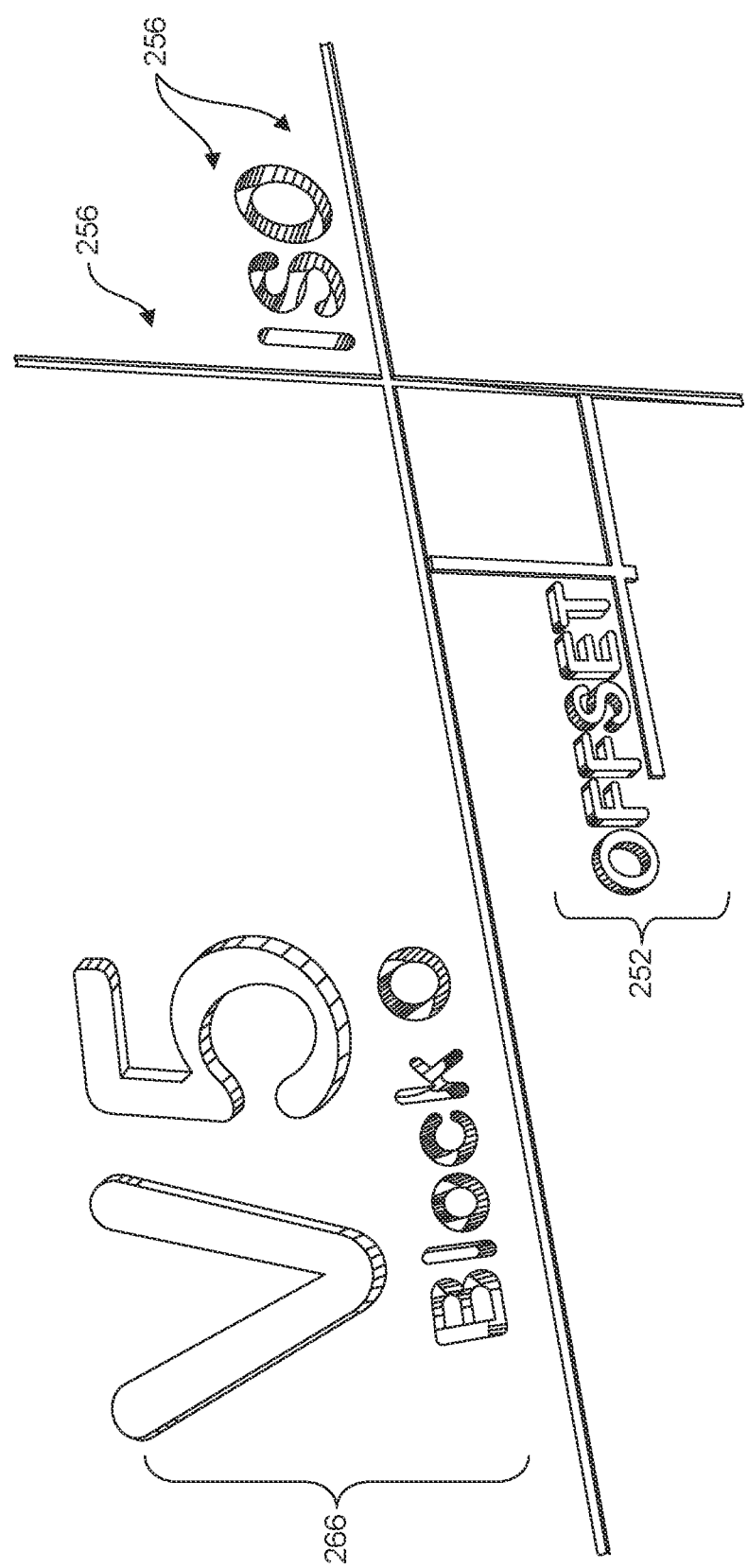
FIG. 2 illustrates Exemplary registration structures/marks, isocenter and offset marks according to an aspect of the present disclosure.

The phantom according to principles of the present disclosure may include a unique registration structure on any or all faces. As illustrated in FIG. 1, each of the top face 120, the first side face 128 and the first end face 136 includes an exemplary registration structure. For example, an exemplary registration structure 166 is shown at the first side face 128 of FIG. 1 as "V5" and "Block O". Unique registration structures help with automatic registration, e.g., by algorithm, of the LINAC via the control console (not shown). As illustrated, an exemplary registration structure 166 may be text characters, but is not so limited. The illustrated embodiment includes a registration structure on each of the top face 120, the first side face 128, the second side face 132 (not shown), and the first end face 136. The actual text of the registration structure can be varied, as long as the registration structure includes depth. Registration can be improved if the registration structures includes some or all of the following characteristics: depth, angles, curves, and asymmetry. Exemplary registration structures/marks 266 with isocenter 256 and offset marks 252 are shown in detail in FIG. 2.

Figure 5:
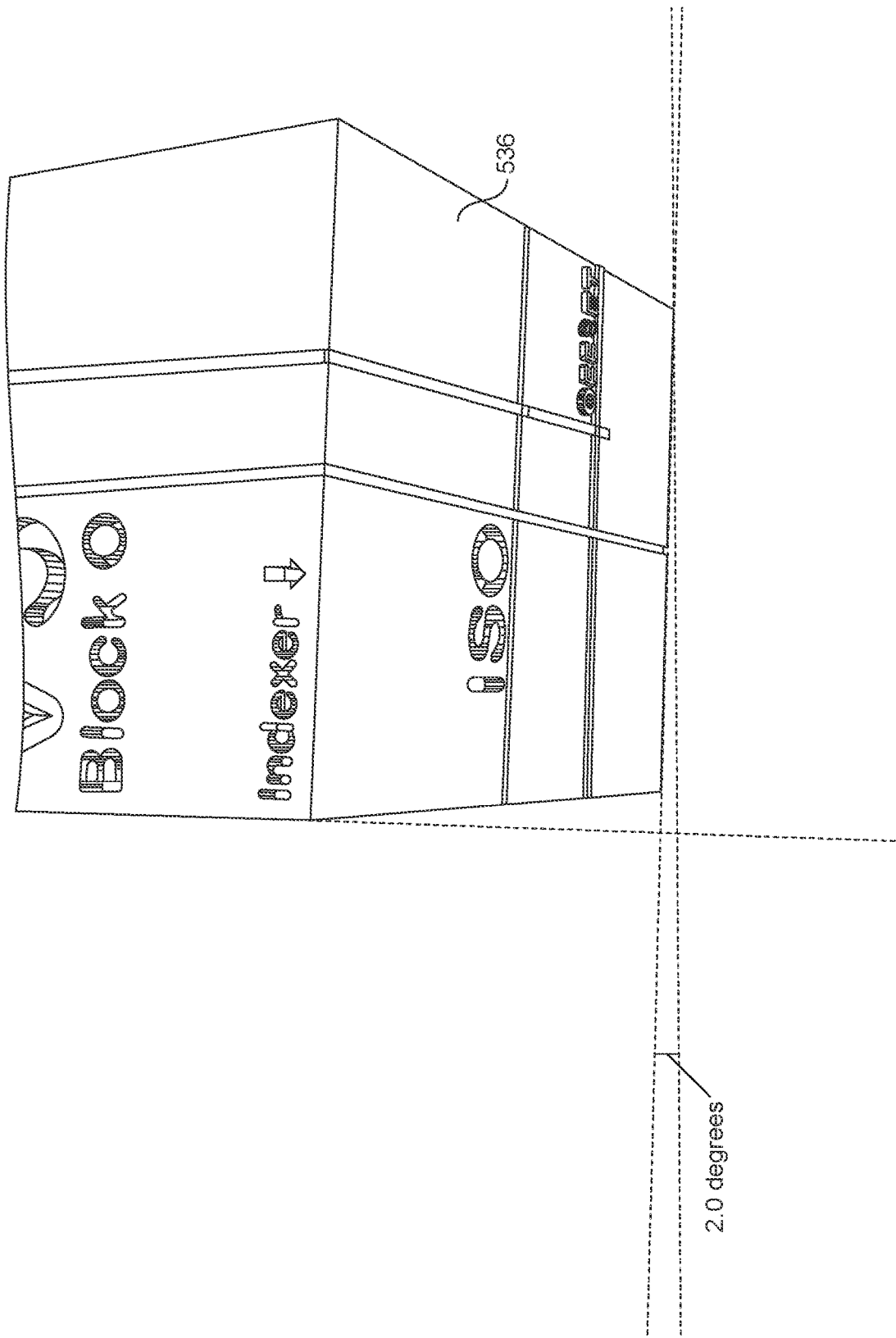
FIG. 5 illustrates an offset from a true rectangular prism of an end face according to an aspect of the present disclosure.
Figure 6:
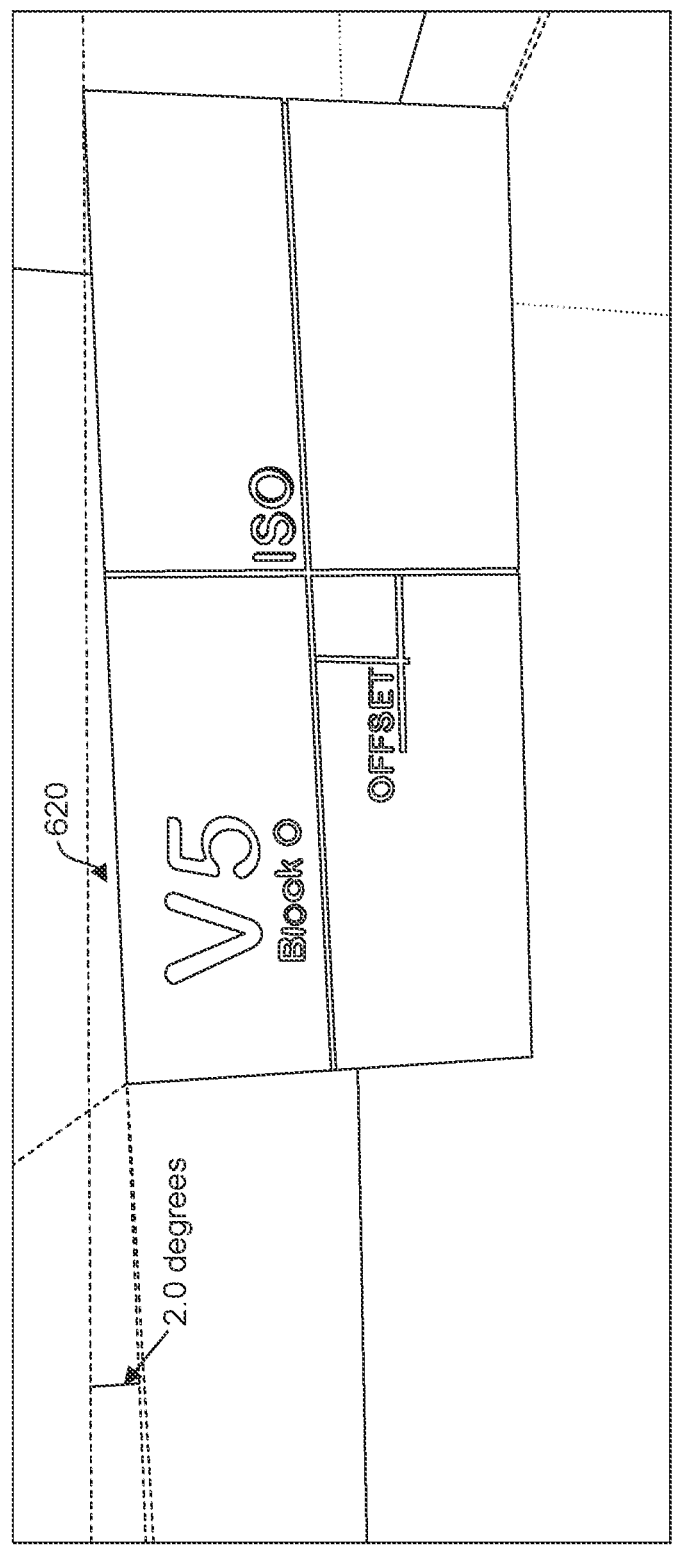
FIG. 6 illustrates an offset from a true rectangular prism of a top face according to an aspect of the present disclosure.

As mentioned above, a phantom according to principles of the present disclosure is rectangular in general, but at least some of the faces of the prism are offset from right angles. The offset can be in a range from 0.5 to 3 degrees. FIG. 5 illustrates a 2° offset from a true rectangular prism of an end face 536. FIG. 5 and FIG. 6 illustrate a 2° offset from a true rectangular prism of a top face 620.

Figure 7:
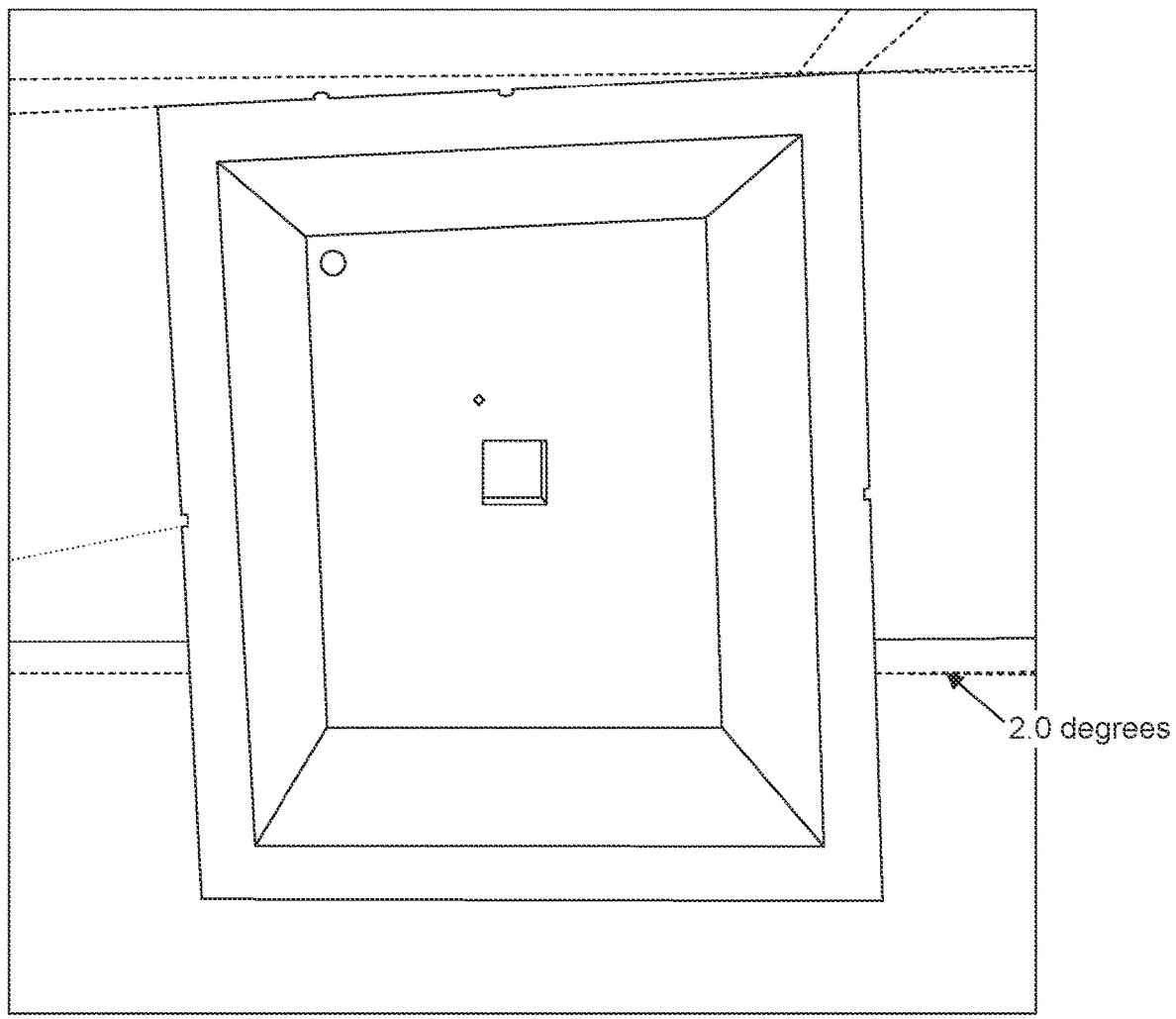
FIG. 7 illustrates a cavity for placement of the ball bearing in the prototype.
Figure 8:
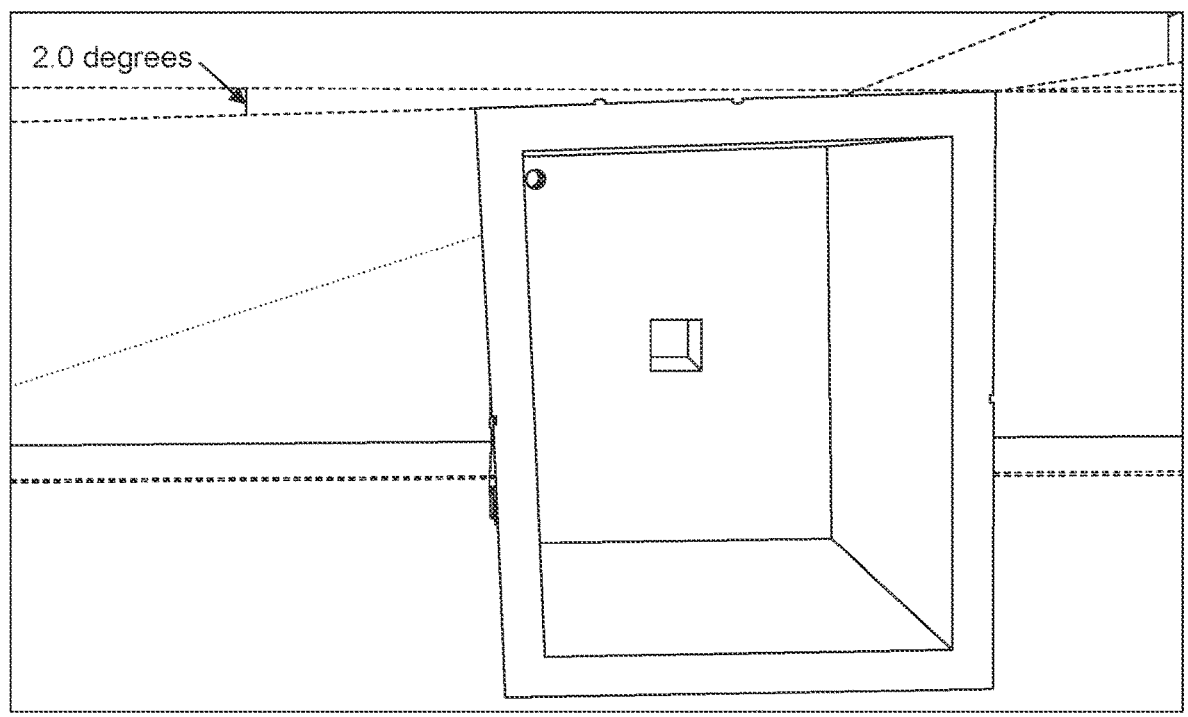
FIG. 8 illustrates top face offset with respect to the ball bearing placement.

The phantom may be solid or hollow or some variation thereof. For example, a prototype of the phantom was made to be partially hollow to allow for manual placement of a ball bearing at the center of the phantom for isocentricity testing. However, formation of the phantom is not limited to 3D printing with manual placement of the ball bearing. The phantom may be formed of any suitable method appropriate for the type of material making up the phantom. For example, the phantom may be injection molded, in which case the ball bearing may be placed at the center of the phantom prior to molding such that the ball bearing is surrounded by or held in place by injection molded material. FIG. 7 illustrates a cavity for placement of the ball bearing in the prototype. FIG. 8 illustrates top face offset with respect to the ball bearing placement.

Figure 9:
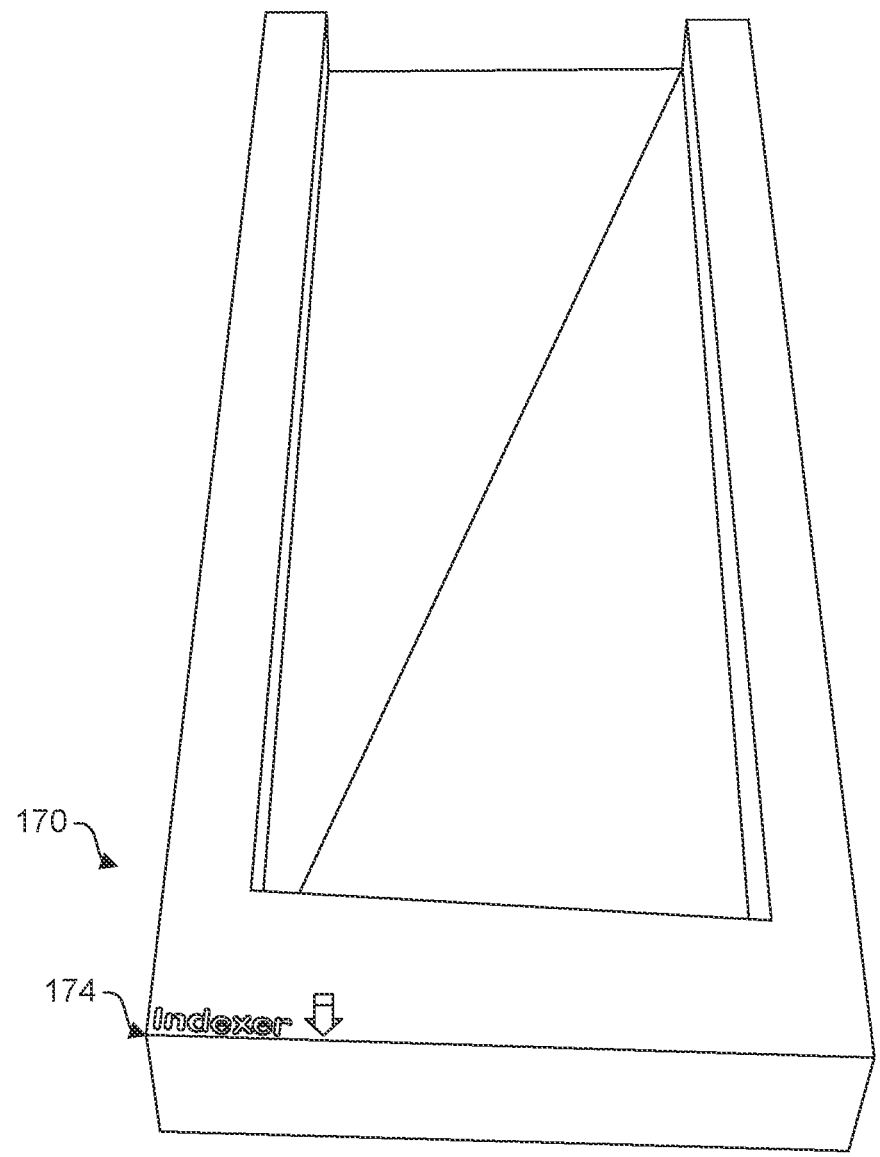
FIG. 9 illustrates and exemplary indexer/leveler according to an aspect of the present disclosure.
Figure 10:
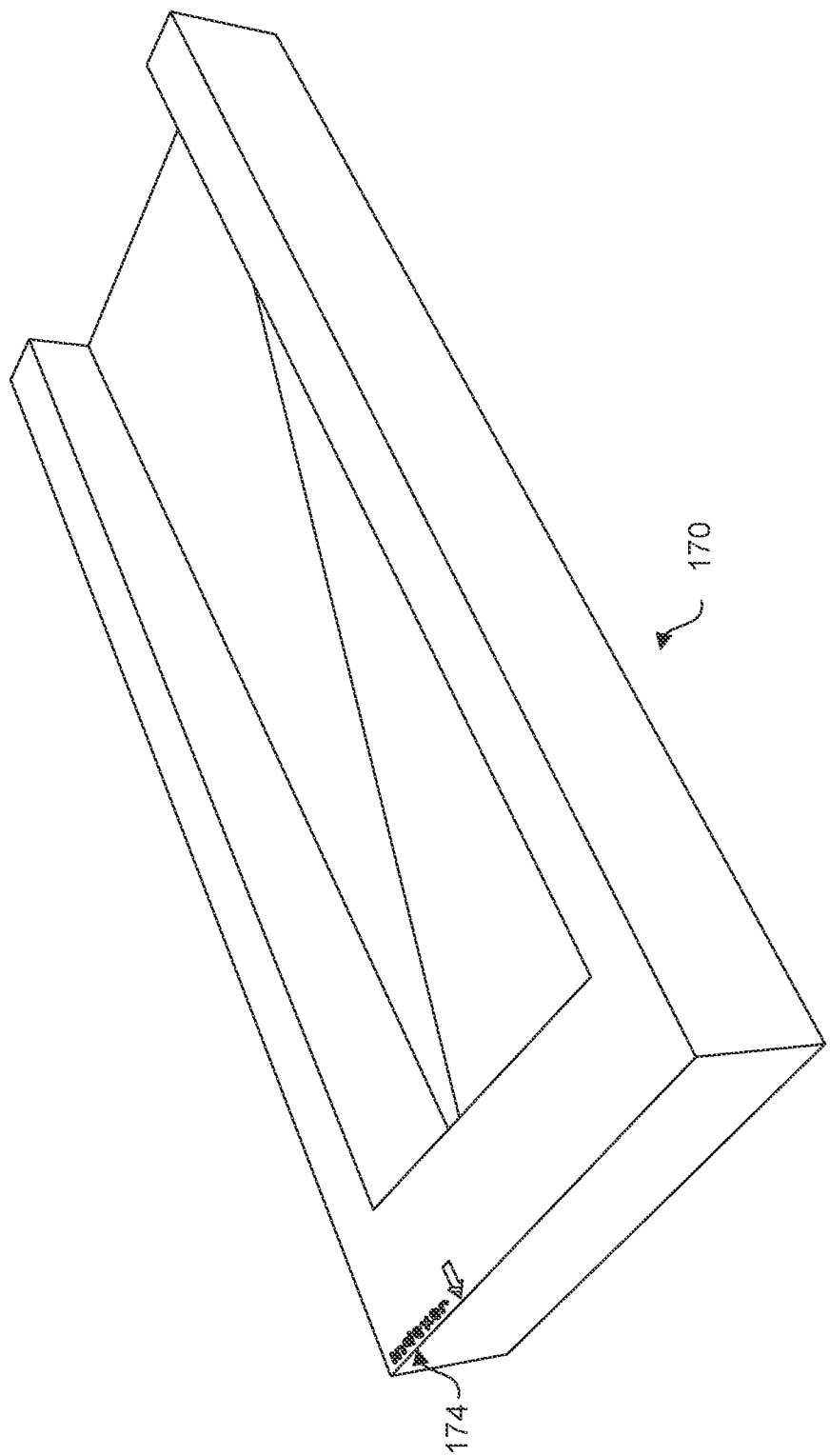
FIG. 10 illustrates and exemplary indexer/leveler according to an aspect of the present disclosure.
Figure 11:
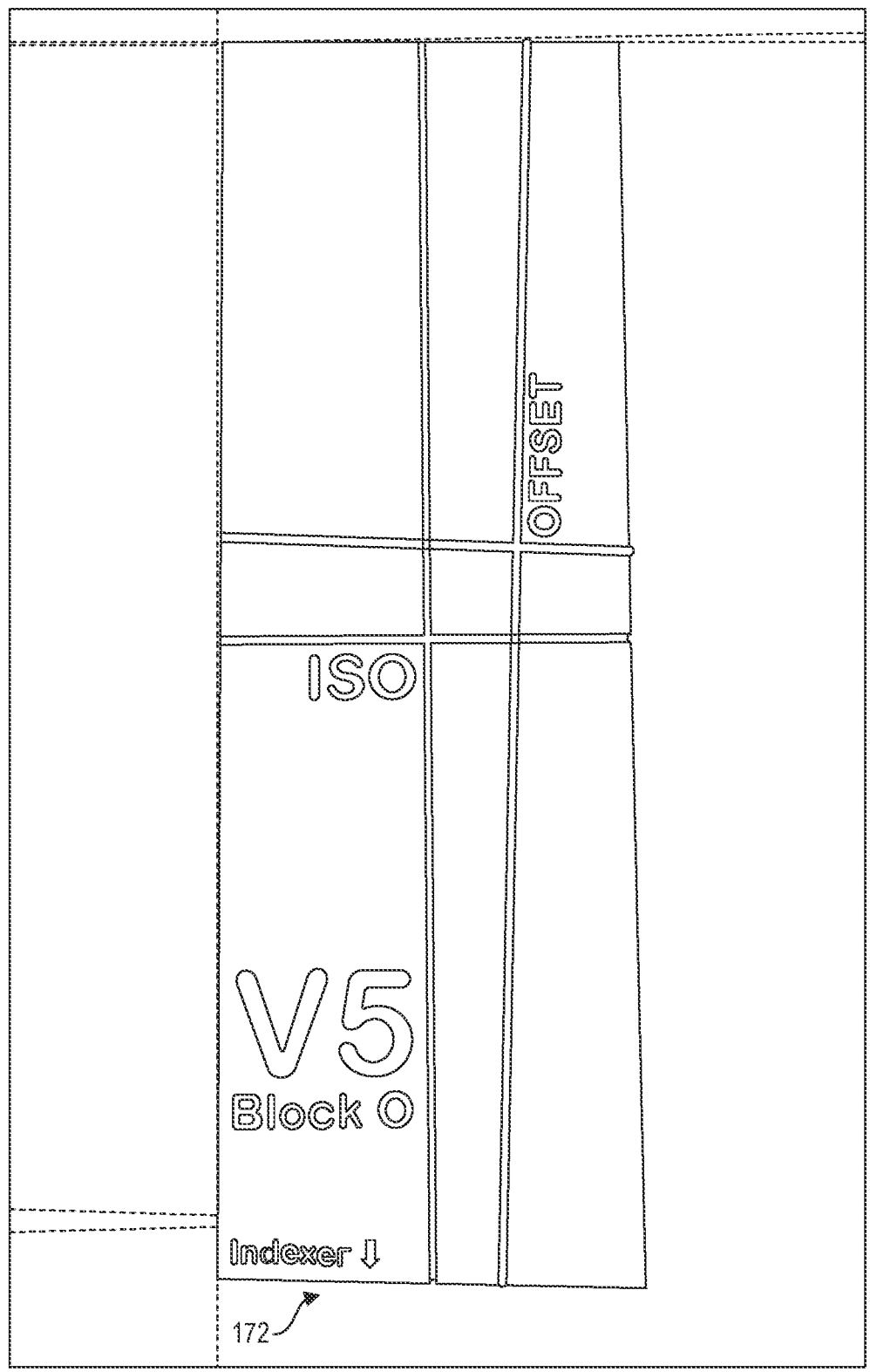
FIG. 11 illustrates an indexer alignment mark according to an aspect of the present disclosure.

A leveler for the phantom may be provided to help position a patient treatment device (or the phantom) on a treatment table to help align the phantom on the treatment table. For example, the leveler is used to straighten the 6DoF phantom for reference imaging purposes. The phantom sits in the leveler and abuts a table indexer, and reference imaging is taken to provide 6DoF adjustments at the LINAC. An exemplary leveler 170 for use with the phantom is illustrated in FIG. 9 and FIG. 10. As illustrated in FIG. 11, an indexer alignment mark 172 may be included in the phantom to assist in an alignment of the phantom on the leveler, specifically with the yaw rotation. A complementary indexer alignment mark 174 is seen in FIG. 9 and in FIG. 10.

A prototype phantom was created using a computer aided design (CAD) software and converted into a language compatible to our department 3D printer. The printer uses fused deposition modeling (FDM) in what would be typically called a "hobby" or "desktop" printer. The design includes known angulation to the faces of the print in order to correct for skewness during QA testing. At the center of the phantom, a ball bearing (BB) was placed for isocentricity testing, which tests the coincidence between the mechanical and radiation isocenter (coordinate origin). With a straight reference image taken at simulation (using 3D printed leveler to straighten device), the phantom is volumetrically imaged at an offset position and angulation. During image registration, the phantom is corrected using an iterative registration algorithm that adjusts the phantom for rotation and translation based on the aligned reference image. The novelty of this design is not only that it efficiently tests the new 6DoF technology, but it also consolidates several additional regulated daily tests.

Imaging for a subject 6DoF table using a phantom according to principles of the present disclosure involved first creating an initial data set by placing the 6DoF phantom in the leveler and abutting to a table indexer on the computed tomography (CT) table. The CT room lasers are lined up with the isocenter marks on the phantom, and the phantom image that is acquired using the associated CT scanner is generated to create the initial data set (reference image). Once a plan is generated using the reference image and localizing the isocenter to the center of the ball bearing (BB), periodically, e.g., daily, the phantom is placed on the 6DoF table abutting the indexer but now without the leveler, and the LINAC lasers are lined up with the offset marks on the phantom. A cone-beam CT (CBCT) scan is performed and registration is conducted to generate a shift/displacement profile to correct for translations in the lateral, longitudinal, and vertical direction and rotations in the pitch, yaw, and roll of the 6DoF table. The shifts are applied in order to move the table via appropriate registration algorithm (which can be commercial software, for example) and the shifts can be verified by checking the alignment with the isocenter marks with respect to the laser, which should line up if the expected shifts have been implemented for the 6DoF table. The final position at the isocenter marks will be aligned to the center of the phantom where the BB is located.

Since 6DoF technology is relatively new, a phantom for 6DoF for QA testing is limited. Using computer aided design software, skewed angulation was developed to test rotational correction into the phantom design. Furthermore, unique registration structures that aid in the automatic registration algorithm were added for use in image guidance setup. Three phantoms were printed for three different exemplary linear accelerators for proof of concept and provided accurate and reproducible results. These results fall within regulated tolerances for multiple daily linear accelerator tests.

To establish a streamlined end-to-end test of a 6 degrees-of-freedom (6DoF) robotic table using a 3D printed phantom for periodic quality assurance, a 3D printed phantom was fabricated with translational and rotational offsets and an imbedded central ball-bearing (BB). The phantom underwent each step of the radiation therapy process: CT simulation in a straight orientation, plan generation using the treatment planning software, setup to offset marks at the LINAC, registration and corrected 6DoF table adjustments via hidden target test, delivery of a Winston-Lutz test to the BB, and verification of table positioning via field and laser lights. The registration values, maximum total displacement of the combined Winston-Lutz fields, and a pass or fail criterion of the laser and field lights were recorded. The quality assurance process for each of the three exemplary LINACs were performed for the first 30 days. Results: Within a 95% confidence interval, the overall uncertainty values for both translation and rotation were below 1.0 mm and 0.5° for each exemplary LINAC, respectively. When combining the registration values and other uncertainties for all three exemplary LINACs, the average deviations were within 2.0 mm and 1.0° of the designed translation and rotation offsets of the 3D print, respectively. For all three exemplary LINACs, the maximum total deviation for the Winston-Lutz test did not exceed 1.0 mm. Laser and light field verification was within tolerance every day for all three exemplary LINACs given the latest guidance documentation for table repositioning. Conclusion: The 3D printer is capable of accurately fabricating a quality assurance phantom for the purpose of 6DoF positioning verification. The end-to-end workflow allows for a more efficient test of the 6DoF mechanics while including other important tests needed for routine quality assurance.

The robotic patient positioning table is an important component in external beam radiation therapy treatments. These tables can mechanically drive a patient to a desired treatment position with the aid of external skin marks or fiducials. Furthermore, most modern linear accelerators (LINACs) are equipped with two- or three-dimensional image guidance in order to correct for and minimize inter-fractional setup uncertainties. Image-guided radiation therapy (IGRT) has improved accuracy for daily treatments and have allowed clinicians to decrease planning target volumes in order to spare normal tissues.[1] However, with LINAC-based treatments demanding greater accuracy, quality assurance (QA) tolerances for image-guidance and table positioning must be in congruence with more precise treatments. The American Association in Physicists in Medicine (AAPM) task group report 142 (TG-142) regarding quality assurance on medical accelerators specifies these tolerances with the type of treatment being delivered, especially with more complex modalities like intensity modulated radiation therapy (IMRT), stereotactic radiotherapy (SRT) and stereotactic body radiation therapy (SBRT).[2]

Conventional treatment tables are designed with four degrees-of-freedom (4DoF) in order to adjust positioning in the patient's vertical, lateral, and longitudinal directions, as well as an additional yaw rotation. A relatively new technology that is being outfitted on LINACs are robotic six degrees-of-freedom (6DoF) tables that allow for mechanical adjustments of pitch and roll rotations in addition to the standard 4DoF adjustments. Early work in 6DoF corrections was investigated using BrainLAB's ExacTrac 6D system (BrainLAB AG, Feldkirchen, DE). BrainLAB utilizes a stereoscopic x-ray system with 2D-to-3D registration system to reference digitally reconstructed radiographs (DRR). 6DoF registration showed a superior submillimeter localization accuracy against 3DoF registration using a head phantom.[3] Rotational corrections with the Robotic Tilt Module on the Exactrac system showed an overall accuracy of 0.31±0.77 mm with a quadrature summation of positional accuracy and isocentricity uncertainty.[4]

Takemura et al. analyzed the 3D error vectors for a HexaPOD evo table (Elekta, Stockholm, SE) with and without a 60 kg weight and concluded 55 that the additional weight did not affect the accuracy of the 6DoF positioning.[5]

Clinical indications of on-line rotational adjustments have also been investigated. A theoretical study of rotational corrections by Ayan et al.[6] showed that depending on the shape of the target volume, the effect of not-correcting rotational mismatches could be very detrimental dosimetrically. Both Gevaert et al.[7] and Dhabaan et al.[8] 60 noted improved dosimetric quantities for intracranial stereotactic patients when using 6DoF corrections compared to 4DoF. 6DoF analysis of prostate treatments showed more variability. Chiesa et al. noted minimal dosimetric impact for spherical prostate targets with 6DoF corrections but potentially significant dosimetric deviations for elongated targets with seminal vesicle involvement.[9] Other prostate studies observed rotational adjustments greater than 2° and commented on the importance to correct for larger deviations.[10,11] Two studies categorized 6DoF accuracy in terms generalized disease sites. Guckenberger et al. compared 6DoF setup accuracies in terms of non-fixated immobilization (body) and fixated immobilization (cranial or head and neck).[12] Schmidhalter et al. classified 6DoF accuracies by cranial and extracranial treatments.[13] In both studies, it was observed that extracranial, or body-type, treatments required a larger translational and rotational correction. While clinical implementation of 6DoF tables yield more accurate image-guided results, routine QA for 6DoF tables has been limited. Schmidhalter et al. has demonstrated reproducible 6DoF table performance using a combination of graph paper, inclinometers, and imaging methods.[14] These tests have demonstrated a process in which routine QA for 6DoF tables can be established. While 6DoF commissioning and QA have been characterized by other studies, it is to the best of our knowledge that a streamlined procedure has yet to be developed. One such technology that is capable of establishing an efficient workflow is 3D printing. This "relatively new, rapidly expanding" technology has advanced personalized medicine by developing customized prosthetics, models, and medical devices.[15] Tack et al. provided a systematic literature review regarding 3D printing publications in medicine.[16] They observed a rapid rise in publications after January 2011, with a majority of the publications originating from the surgical domain in medicine. This can be exemplified by such work on 3D printed frames for laser interstitial thermotherapy[17], creating 3D anatomical models from magnetic resonance imaging[18], and accurately printing organs with heterogeneous tissues.[19] Moreover, the emergence of 3D printing technology in various arenas in medicine has garnered similar interest in radiation oncology. A significant amount of effort into 3D printing has been utilized for patient-specific devices, which include: bolus for electron treatments[20-22], compensators for photon treatments[23,24], and patient immobilization[25]. 3D printing in brachytherapy applicators has also been investigated. Dosimetric evaluations of an FDA approved material[26] and various material infill densities[27] has shown promising results. 3D printed phantoms have also been successfully developed for various QA demands. Ehler et al. fabricated an anthropomorphic phantom to test the feasibility of rapid prototyping for patientspecific QA.[28] Madamesila et al. characterized the variable density of 3D printed samples as a function of percent material infill that focused on densities in the lung range.[29] From a machine based QA perspective, Bieniosek et al. compared a 3D printed replication of a commercial PET/CT phantom to the commercial phantom itself.[30] In terms of LINAC-based QA, little effort has been explored in creating 3D printed models to meet specific QA purposes. The aim of this work is to determine the feasibility of generating a 3D printed QA phantom in order to test the accuracy and reproducibility of a 6DoF table alignment. The 6DoF phantom will be constructed such that the tests can be performed in a streamlined fashion. The workflow will be aimed to follow typical end-to-end testing, where it will be CT simulated, planned for isocentric localization, setup at the treatment LINAC, and imaged following stereotactic IGRT protocols. After establishing baseline alignment shifts and isocentricity values, the phantom can be produced by any of a number of techniques and implemented into the daily QA routine.

Materials and Methods

6DoF Table

Tests were performed on three Truebeam LINACs, each equipped with a 6DoF PerfectPitch table (Varian Medical Systems, Palo Alto, Calif.). Based on relative patient coordinates, the mechanical movements possible in traditional 4DoF tables include three translational directions in the left-right (lateral), superior-inferior (longitudinal), and anterior-posterior (vertical) positions, as well as a yaw rotation direction. Newer 6DoF capabilities allow for two additional rotation adjustments which can correct for the patient's pitch and roll. The PerfectPitch table is equipped with additional robotic motors in order to correct for pitch and roll. The pivot point for the attachment is at a different location than the yaw rotation about the machine isocenter. Thus, if only pitch and roll corrections were applied, the treatment isocenter would be rotated away from the mechanical isocenter. Restorative translational shifts need to be applied in order to match back to the mechanical isocenter. These restorative corrections are integrated into the image-guided registration at the console. The mechanical limitations for pitch and roll corrections are ±3.0°.

B. 3D Printer

The 3D printer used was the BCN3D Sigma (BCN3D Technologies, Barcelona, ES). The Sigma model is what is commonly referred to as a relatively low-cost "desktop" or "hobby" printer. The Sigma utilizes a fused filament fabrication (FFF) method of printing. In FFF, a spool of suitable filament material traverses a heated element and is extruded through a small diameter nozzle. During extrusion, the filament is heated past its melting point into an amorphous form and is deposited layer-by-layer, starting from the bottom of the model. Once deposited, the material cools and solidifies into the desired design. The Sigma printer is a dual-nozzle printer, allowing for a single print to be designed with two different materials or colors. The maximum build dimensions for the printer are 21.0×29.7×21.0 cm$^3$. The nozzle diameter utilized was 0.4 mm. The manufacturer quoted nozzle positioning resolution was 12.5 µm in the lateral direction and 1.0 µm with the layer height. The Sigma is also equipped with a heated platform. The heated platform serves two main purposes: to mitigate warping by decreasing the cooling rate of the material and to prevent the build from detaching from the platform. The 3D model was created using a computer-aided design (CAD) freeware program. The final version of the design was saved as a stereolithography (STL) file. Once generated, the STL file was imported into a proprietary 3D printing preparation software and converted into a language compatible for the 3D printer called a GCODE file. A GCODE file is a numerically controlled programming language that gives multivariate instructions regarding printer extruder location, speed, temperature, and rate, along with other printer-specific settings.

C. Establishment of end-to-end test

Figure 12A:
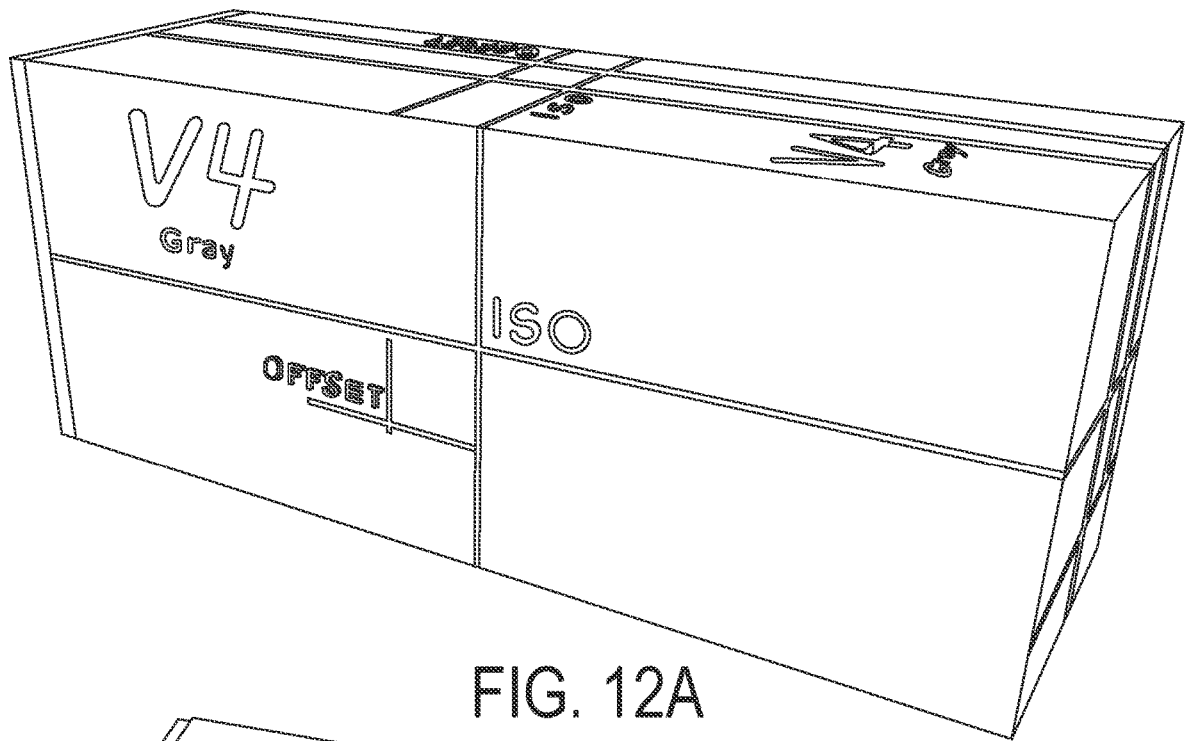
FIGS. 12A-12B show one example of the 3D printed phantoms.
Figure 12B:
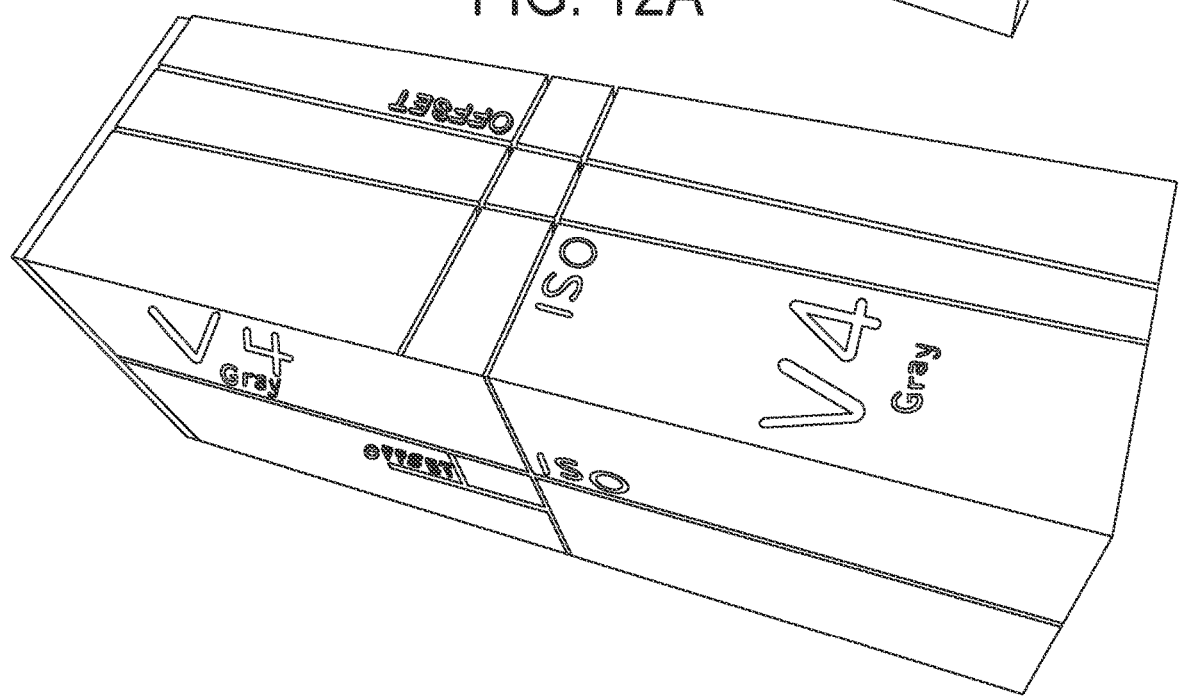

In order to establish a streamlined test for 6DoF registration and mechanical motion, an end-to-end test was devised. FIG. 12 shows one example of the 3D printed phantoms. FIG. 12(a) shows a side and FIG. 12(b) shows a top view of a 3D printed phantom with initial set up marks (OFFSET) and isocenter indicator with ball bearing at the isocenter (not shown). The faces of the print are angled in order to correct for each rotation using the 6DoF couch/table The CAD model was built with known angular and translational offsets for alignment. The faces of the print were designed with 2.0° angular offset for the yaw, pitch, and roll rotations. An additional 3D printed leveler was also fabricated so that the skewed phantom would be leveled when used together in every rotation for reference imaging. Two sets of 1.0 mm wide lines were designed on the faces of the phantom: one for an initial offset alignment and one for final isocenter localization. With a concept similar to a hidden target test, the offset marks were used initially to set up the phantom with the lasers and field light. The offset location was designed to be exactly 1.50 cm away from the isocenter marks in each translational direction. The isocenter marks indicate the center of a 7.92 mm diameter chrome steel ball bearing (BB) that is inserted into the 3D print post-fabrication. With CBCT image-guidance, the registration software should detect the designed rotation and translation corrections from the body of the phantom. In order to facilitate the auto-registration algorithm, unique registration structures were designed into the faces of the phantom. If registered correctly, the laser and field light lines should be coincident with the isocenter lines.

Three models of the 6DoF phantom were printed and customized for the three different exemplary LINACs equipped with 6DoF tables. These phantoms were to be tested on a daily basis. CT imaging for each was performed using a Discovery CT590 RT (General Electric Healthcare, Chicago, Ill.). Each phantom was placed in the leveler for a straight alignment in order to establish a corrected reference image. The leveler was also 3D printed with a low infill percentage such that the registration algorithm would not be effected within the region-of-interest (ROI) of the phantom. The thinnest slice thickness (0.625 mm) was used in order to achieve the highest spatial resolution in the scan plane. The CT images were sent to Eclipse treatment planning system (Varian Medical Systems, Palo Alto, Calif.). A plan with a CBCT setup field and six 3.0×3.0 cm$^2$.

Figure 14:
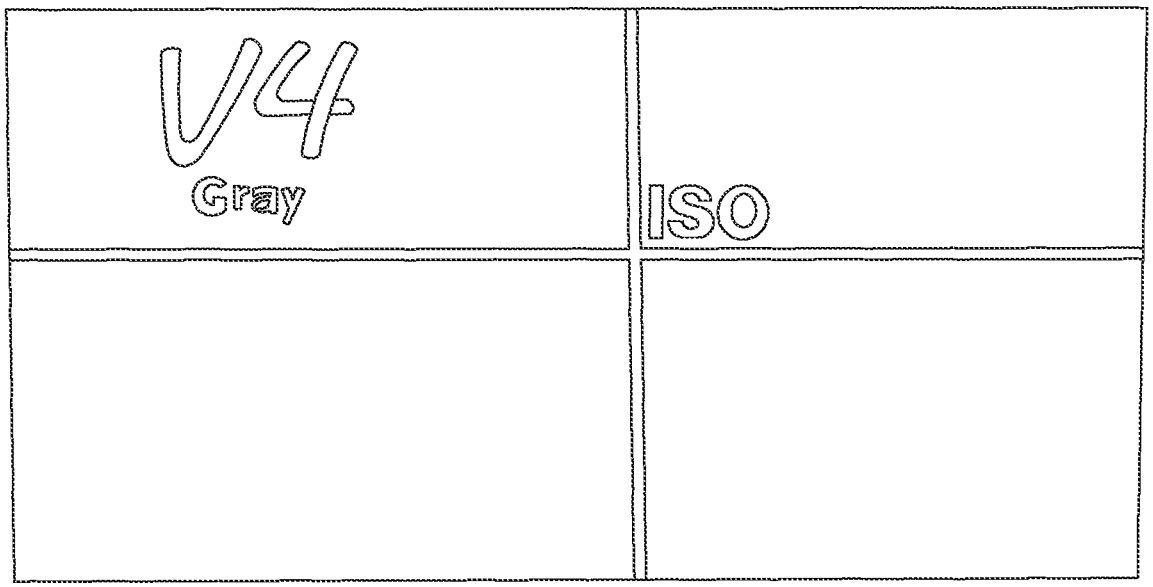
FIG. 14 shows unique registration structures according to principles of the present disclosure.
Figure 15A:
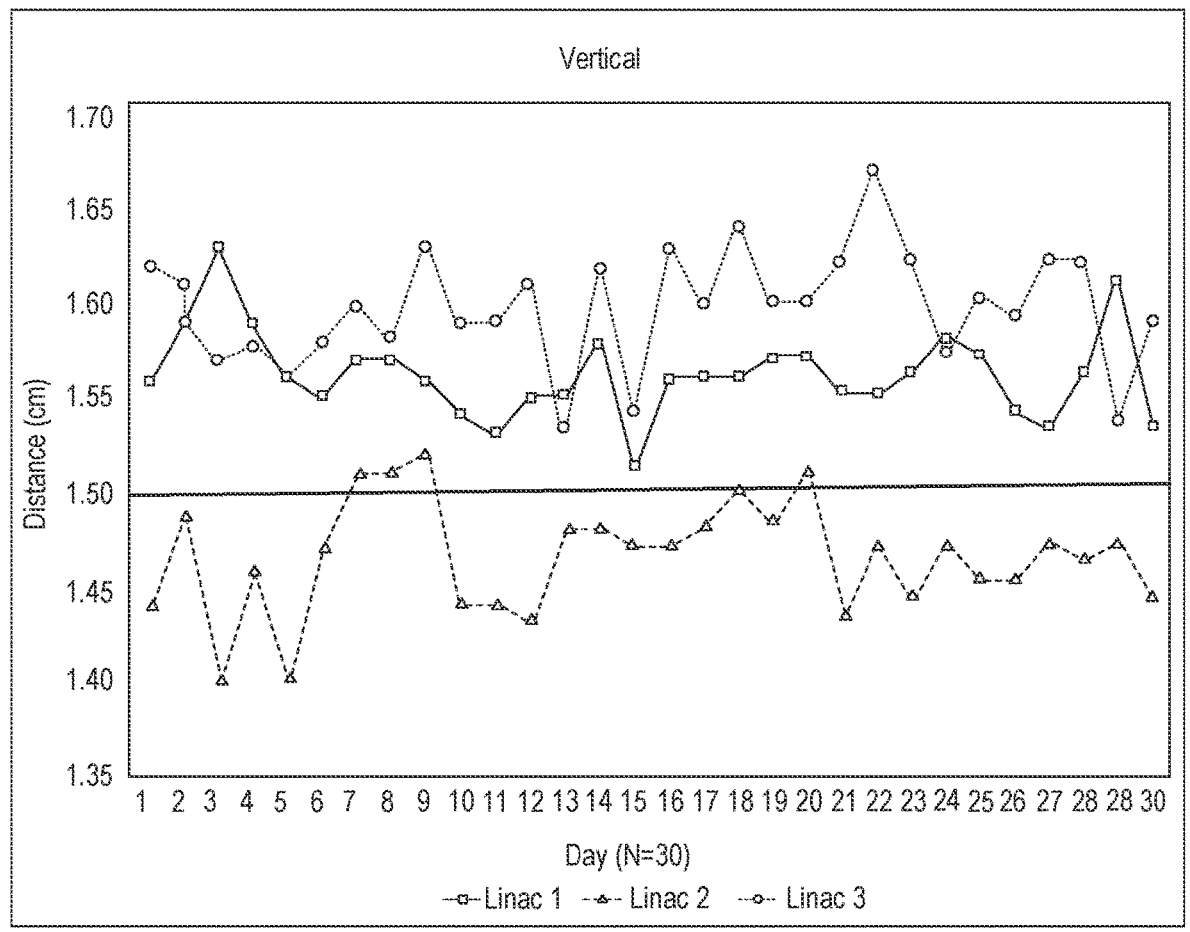
FIGS. 15A-15F show the on-line 6DoF registration values (e.g. vertical at (a), longitudinal at (B), lateral at (c), ditch at (d), roll at (e), and yaw at (f)) for each exemplary LINAC.
Figure 15B:
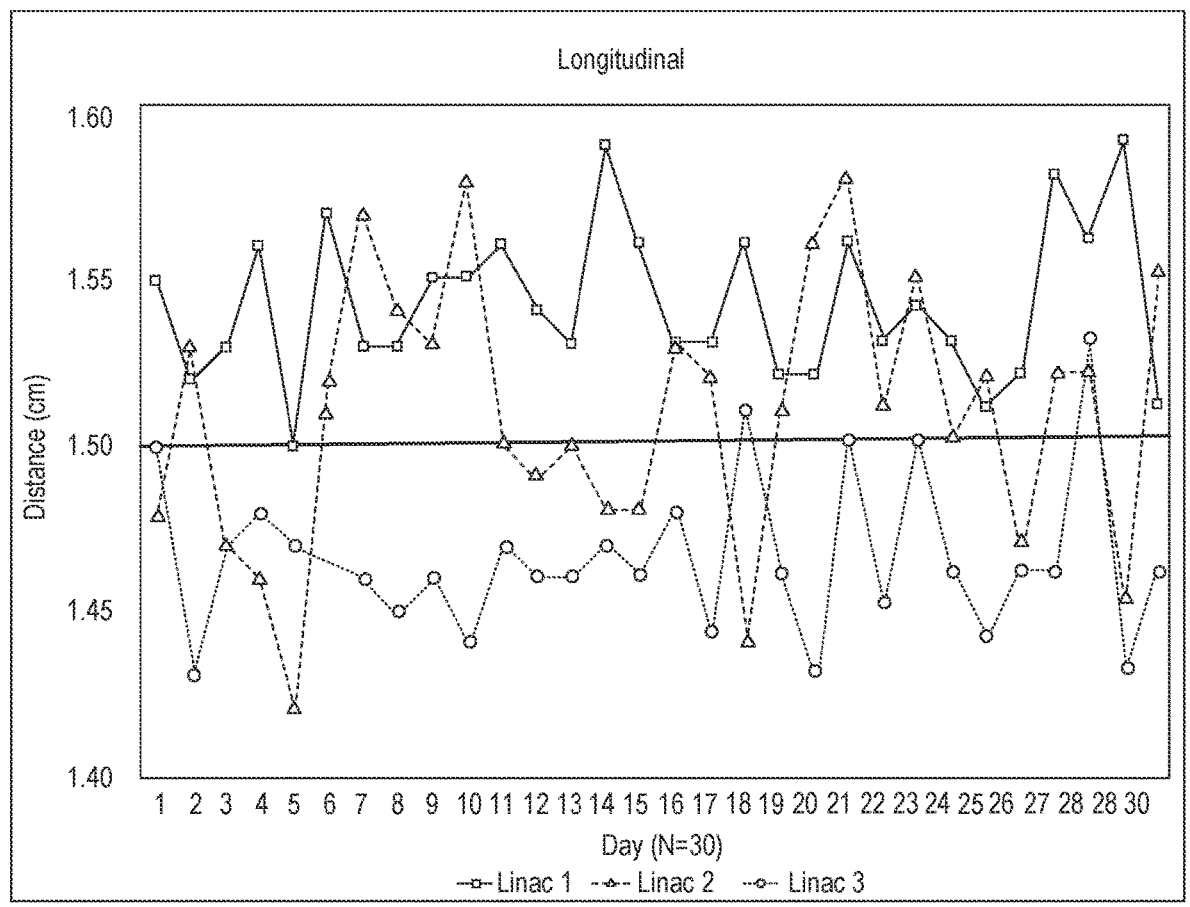
Figure 15C:
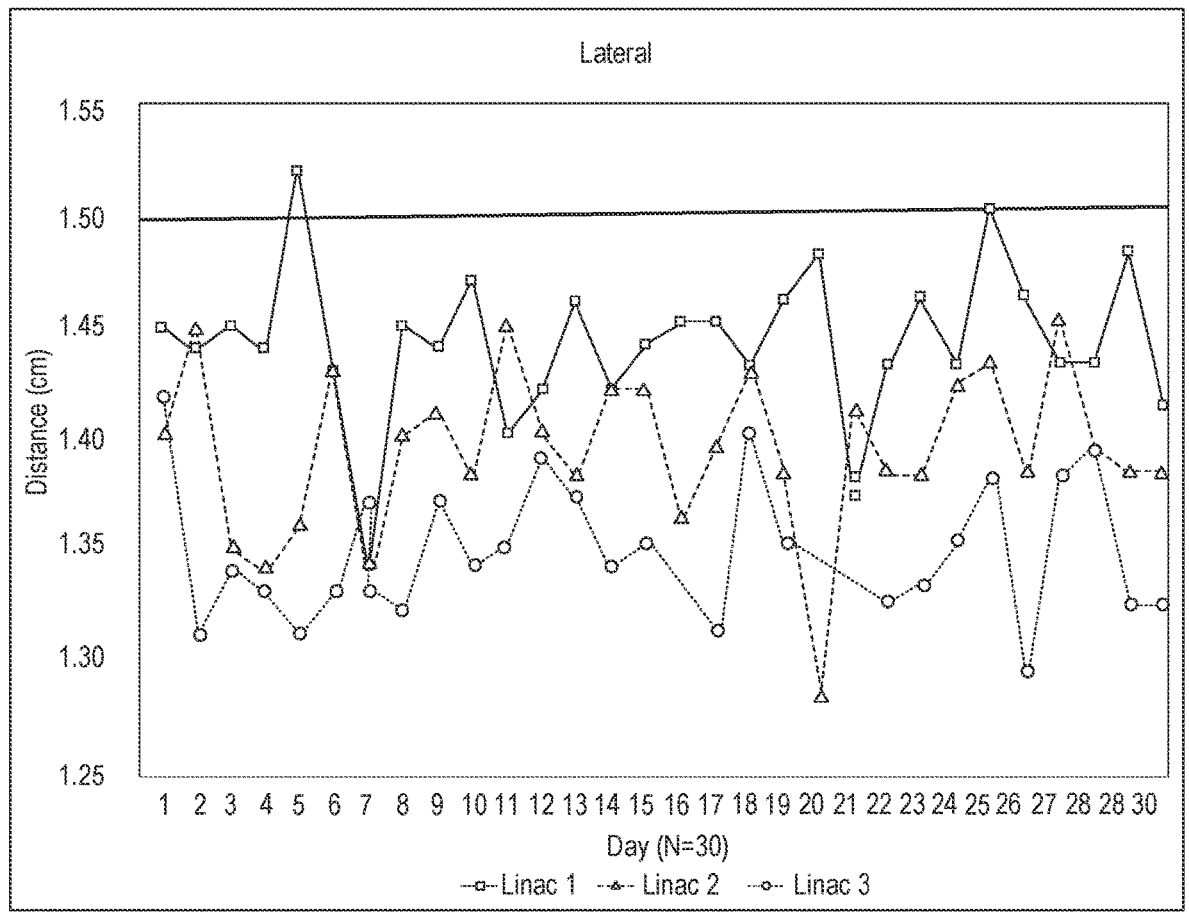
Figure 15D:
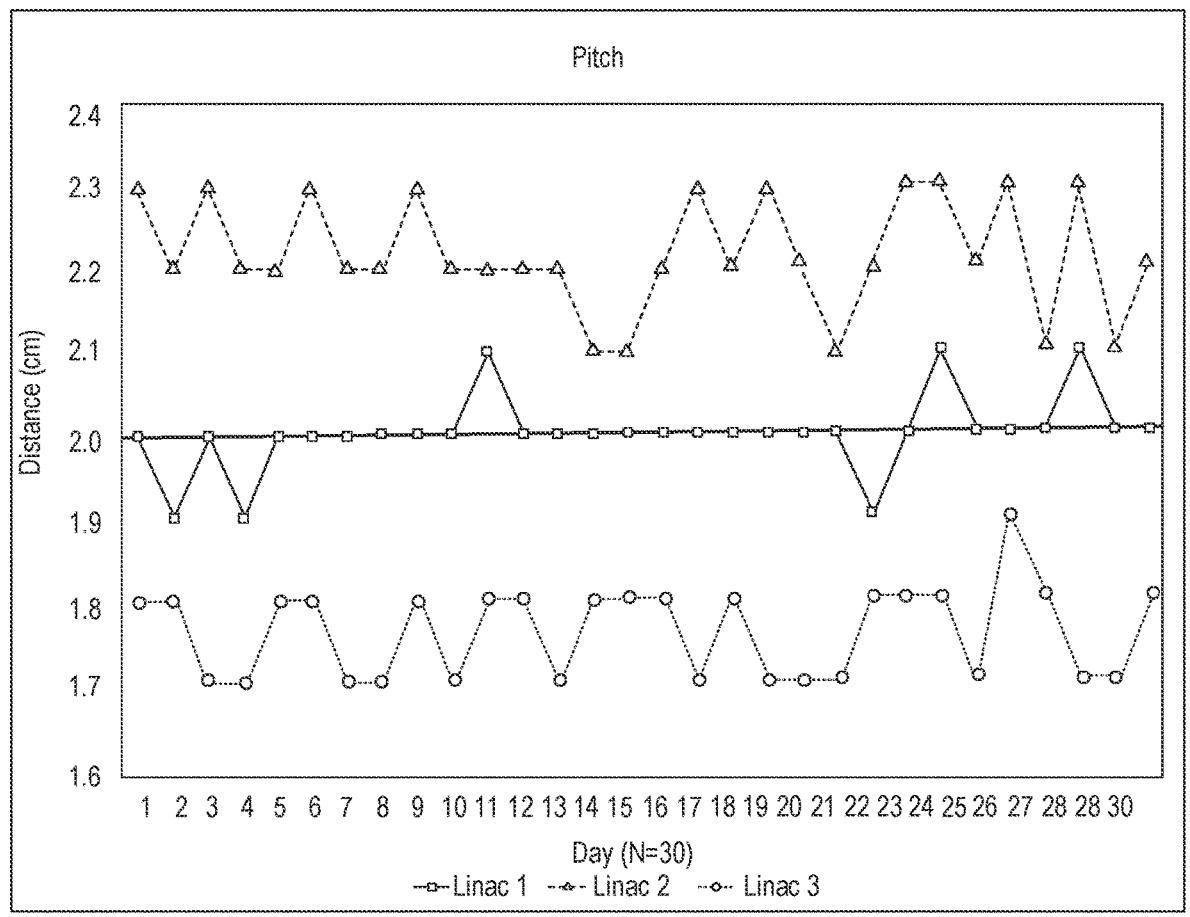
Figure 15E:
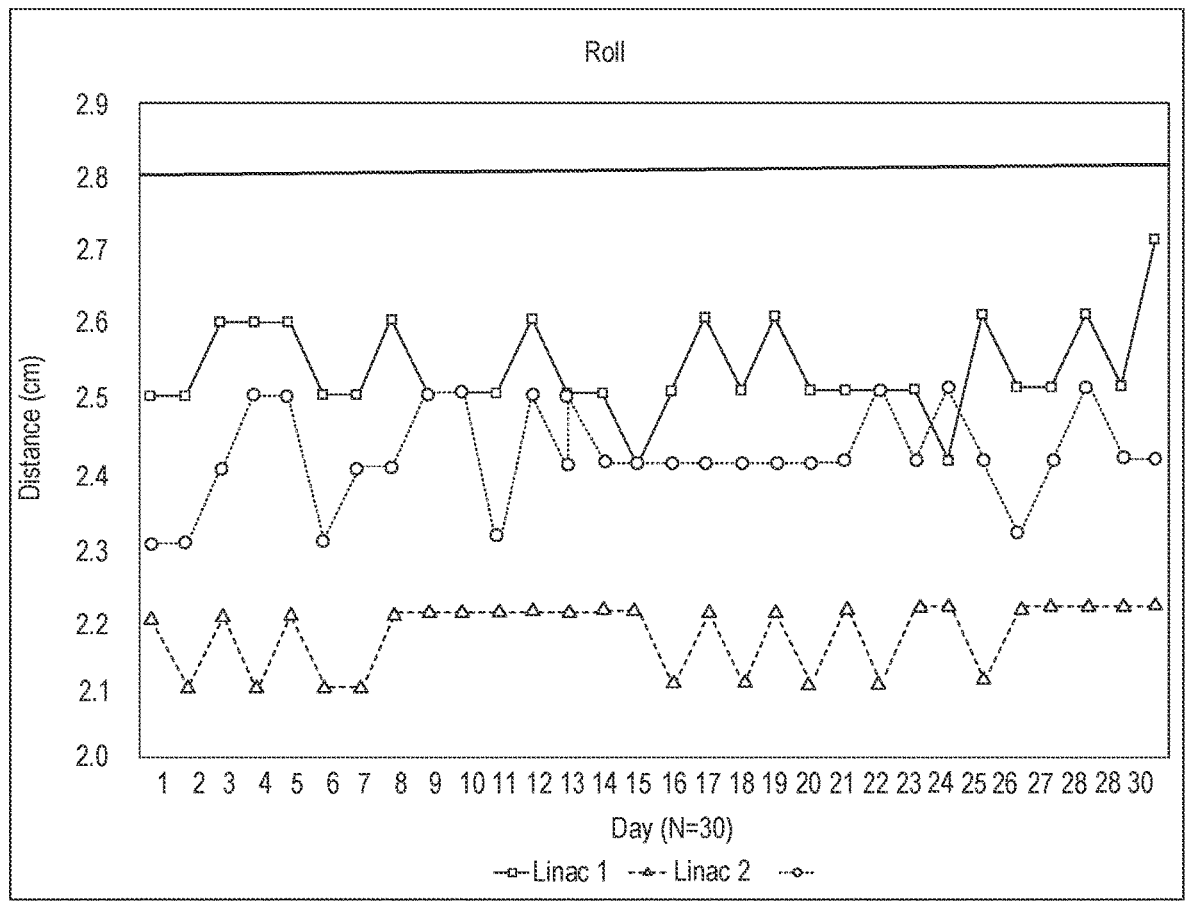
Figure 15F:
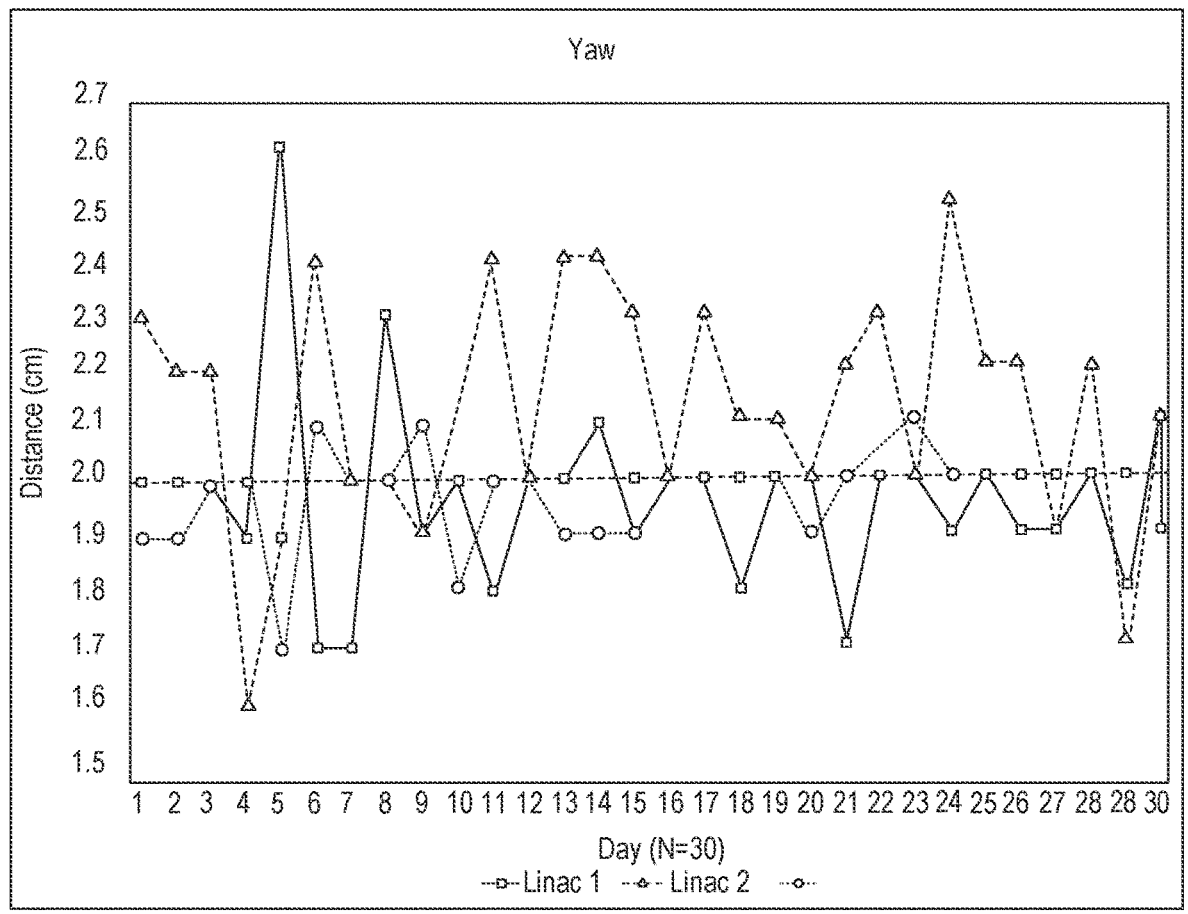

MLC-shaped fields was generated. The six treatment fields were used to deliver a Winston-Lutz (WL) test[31] at the four cardinal gantry angles and two additional collimator angles when the gantry is at 0°. With the leveler removed, each phantom was setup at its designated machine. Each phantom was aligned to the offset lines using the laser and field lights. A table indexer was used in order to place the phantom flush on its end for precise yaw rotation alignment. Once aligned, a halfarc CBCT was taken. FIG. 13 shows the online match of the reference CT and CBCT, that is, an example of on-line CBCT with initial setup of phantom in axial, sagittal, and coronal views at column (a) and adjustments applied using both manual and automatic registration at column (b). A coarse, manual registration was performed only for translation adjustments. Auto-registration was followed for rotational and fine translational adjustments. Unique registration structures were utilized to visually verify the registration (FIG. 14). As shown in FIG. 14, unique registration structures are shown on one face of a phantom according to principles described herein. "V4 Gray" is a nickname for the corresponding LINAC and was intentionally used as the registration structure for the corresponding phantom, although another unique structure could have been used. FIG. 14 also shows an image of the associated leveler/indexer. Translational and rotational shifts were then applied, with the table moving to the center of the BB at the treatment isocenter. Immediately after shifting, the six WL fields were delivered using the electronic portal imaging device (EPID). After WL delivery, laser and field light coincidence was verified with the isocenter lines indicated on the phantom. The WL test was analyzed off-line. The daily end-to-end test was carried out for 30 days for each of the three exemplary LINACs. Shifts for the three translational and three rotational corrections were recorded. The displacement vectors between the center of the BB and the center of the 3×3 cm2 field for the WL tests were measured using the DoseLab Pro software (Mobius Medical Systems, Houston, Tex.). Field and laser light verification was noted with either a pass or fail criteria given TG-142 tolerance.

Results

A. 6DoF Registration

FIG. 15 shows the on-line 6DoF registration values (e.g. vertical at (a), longitudinal at (B), lateral at (c), ditch at (d), roll at (e), and yaw at (f)) for each exemplary LINAC. The dotted black line in each graph represents the designed offset values from the CAD model. Table 1 summarizes the registration data with average 6DoF values of each exemplary LINAC with corresponding uncertainty values of 2 standard deviations (2σ, or 95% confidence interval) for a 30 day data collection period (N=30). For each individual phantom, the 2σ uncertainty was below 0.10 cm for each translational adjustment and 0.5° for each rotational adjustment. Combined data for all three exemplary LINACs was also tabulated in Table 1 (N=90). The combined registration values were 1.54±0.13 cm, 1.51±0.09 cm, 1.39±0.10 cm, 2.0±0.4°, −2.4±0.3°, 2.0±0.4° for the vertical, longitudinal, lateral, pitch, roll, and yaw adjustments, respectively.

TABLE 1

Average registration values for each linac N = 30) with 2σ uncertainty (95$^{th}$ percentile).

| | Vert (cm) | Long (cm) | Lat (cm) | Pitch (deg) | Roll (deg) | Yaw (deg) |
|---|---|---|---|---|---|---|
| Linac 1 | 1.56 ± 0.05 | 1.54 ± 0.05 | 1.44 ± 0.07 | 2.0 ± 0.1 | −2.3 ± 0.1 | 2.0 ± 0.4 |
| Linac 2 | 1.46 ± 0.06 | 1.51 ± 0.08 | 1.39 ± 0.08 | 2.2 ± 0.1 | −2.6 ± 0.1 | 2.1 ± 0.4 |
| Linac 3 | 1.60 ± 0.06 | 1.47 ± 0.05 | 1.35 ± 0.07 | 1.8 ± 0.1 | −2.4 ± 0.1 | 2.0 ± 0.2 |
| Combined (N = 90) | 1.54 ± 0.13 | 1.51 ± 0.09 | 1.39 ± 0.10 | 2.0 ± 0.4 | −2.4 ± 0.3 | 2.0 ± 0.4 |

B. Winston-Lutz Test and Laser/Light Field Verification

Figure 16:
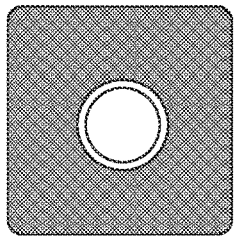
FIG. 16 shows an example of the WL analysis for six field delivery.

An example of the WL analysis for six field delivery is shown in FIG. 16, where G is the gantry angle and C is the collimator angle. The isocenter of the ball bearing is illustrated by a plus sign ("+") and the center of the field size is illustrated by ("X"). By outlining both the field size and BB, the center of each is located and both displacement vectors in the 2D coordinates can be determined at each respective WL field. The total displacement, A, vector for each field is calculated using a simple distance formula between the two central coordinates $$\Delta = \sqrt{\Delta x^2 + \Delta y^2} \quad \text{(Eq. 1)}$$

Δx and Δy represent the displacement vectors for the x and y direction in the planar EPID coordinate system, respectively. The field with the largest Δ would be recorded as the maximum total displacement vector, Δmax, which would be used as the single value for analyzing the displacement between the imaging and radiation isocenter. Δmax values were recorded each day as shown in Table 2.

TABLE 2

Maximum total delta ($\Delta_{max}$) Winston-Lutz values for ach linac (N = 30). Values in mm.

| | Minimum $\Delta_{max}$ | Maximum $\Delta_{max}$ | Average $\Delta_{max}$ | 2σ |
|---|---|---|---|---|
| Linac 1 | 0.55 | 0.98 | 0.69 | 0.20 |
| Linac 2 | 0.69 | 0.94 | 0.81 | 0.14 |
| Linac 3 | 0.49 | 0.77 | 0.62 | 0.14 |

Figure 17:
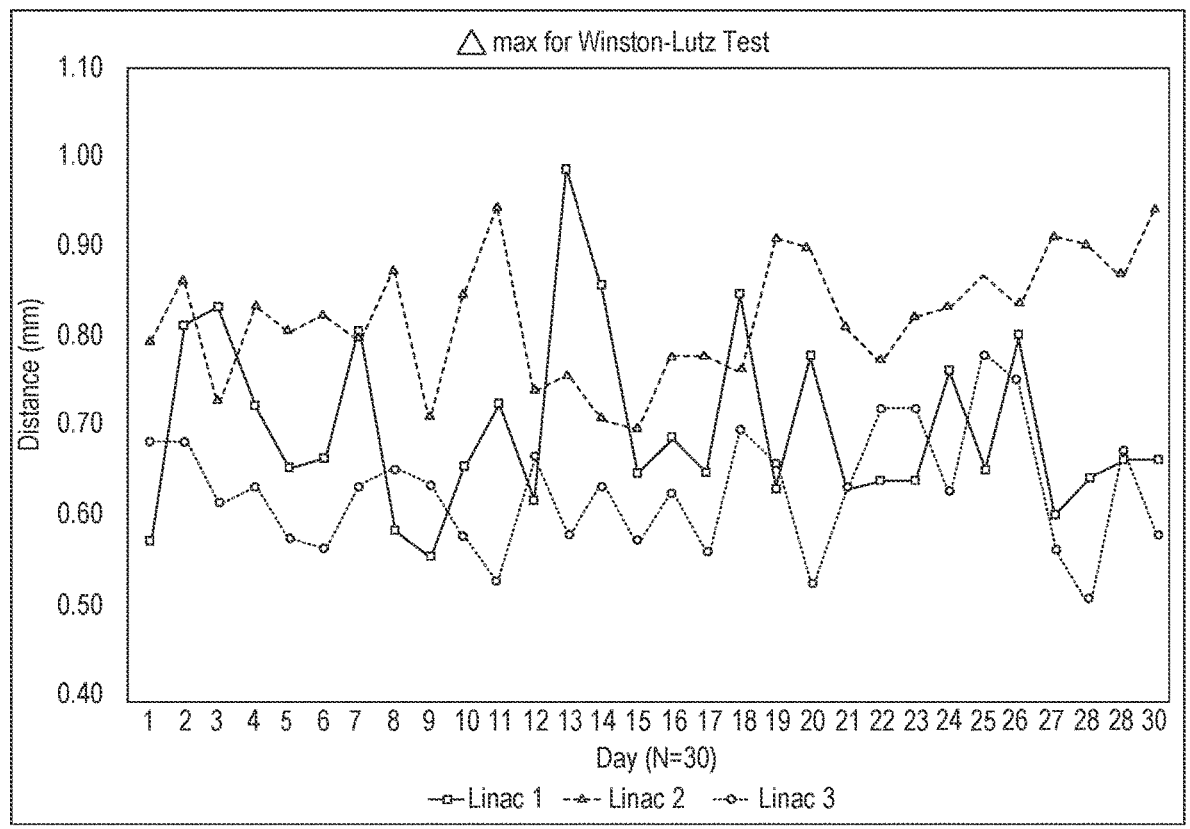
FIGS. 17 and 18 show the Δmax data in a linear and box plot style for each exemplary LINAC, respectively.
Figure 18:
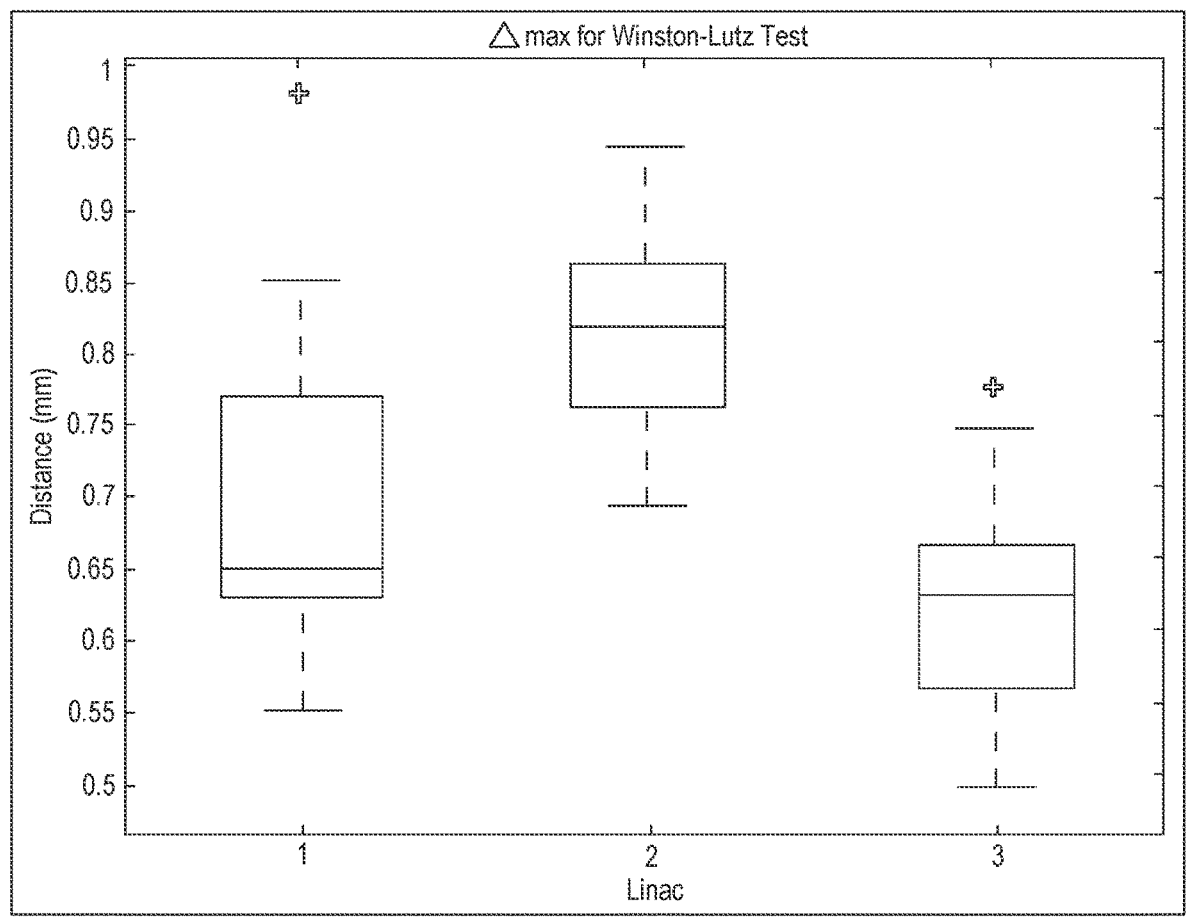
Figure 19:
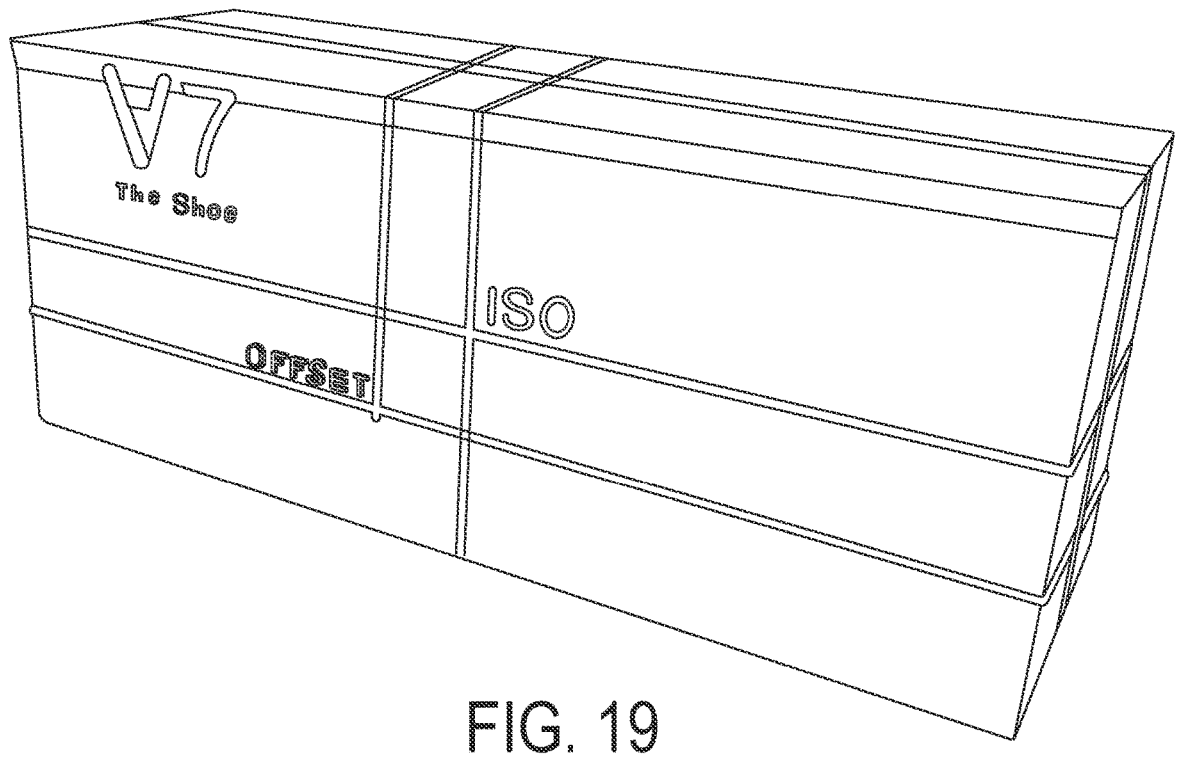
FIGS. 19-35 are photographs of the exemplary phantoms and related indexer/levelers.
Figure 20:
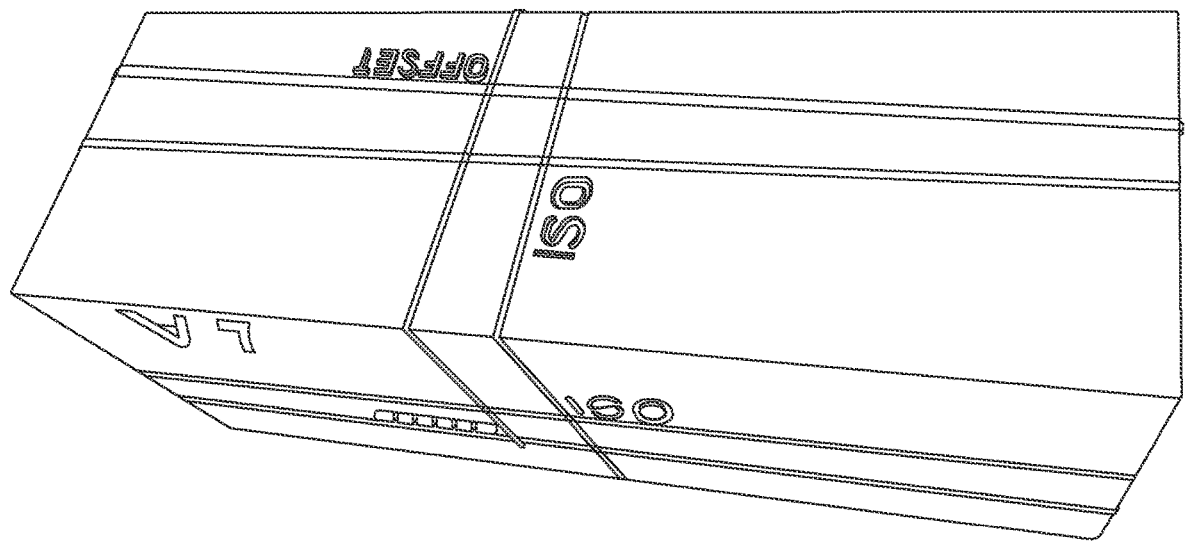
Figure 21:
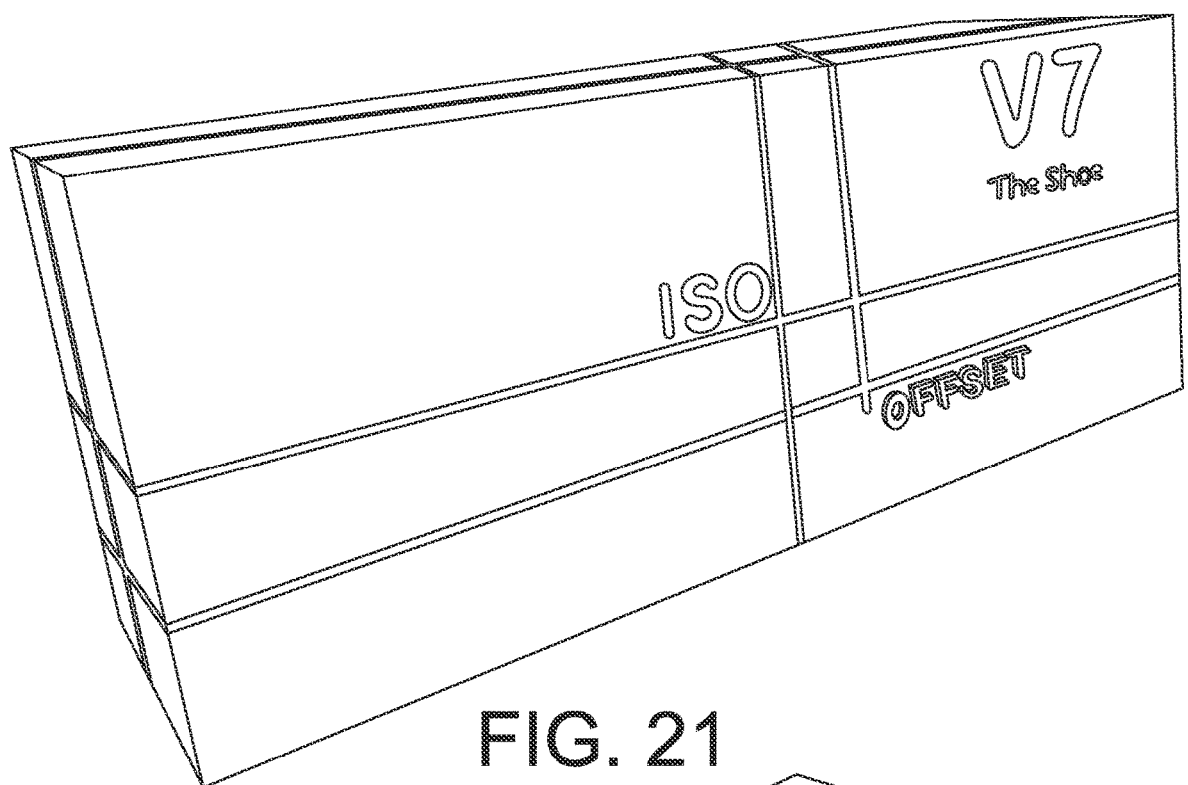
Figure 22:
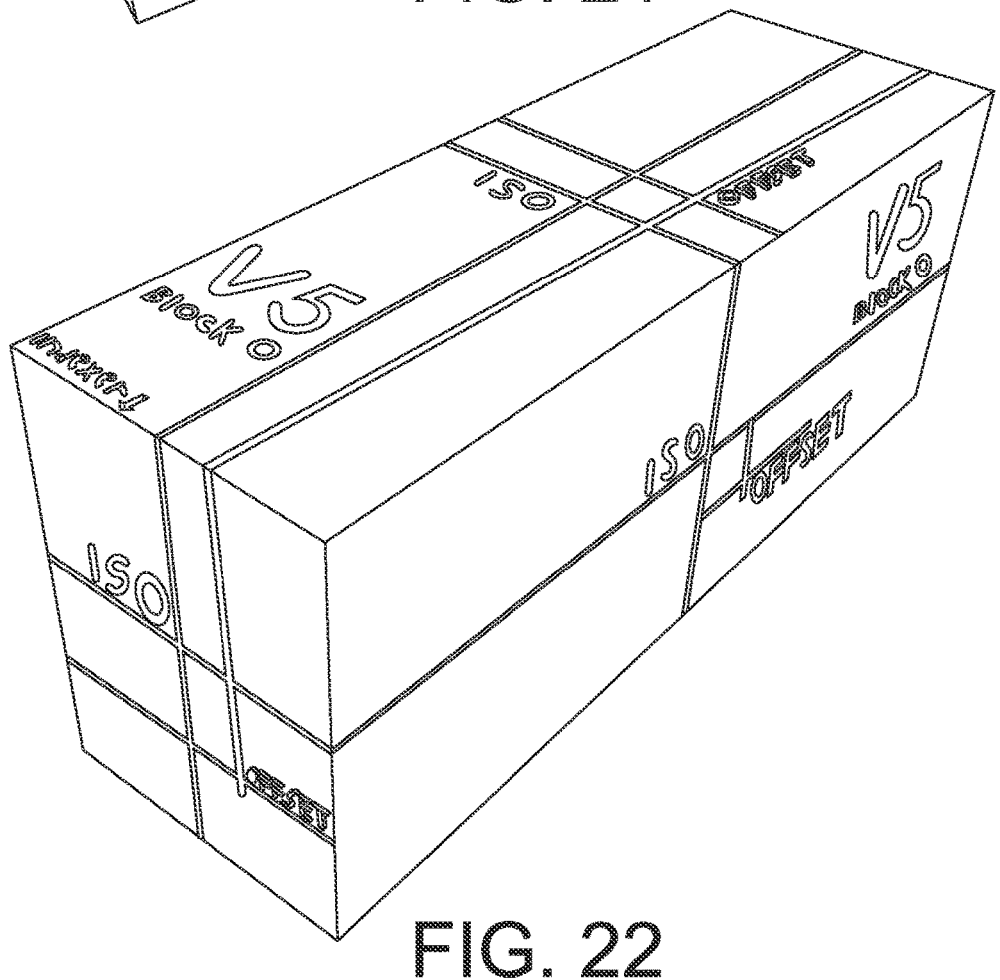
Figure 23:
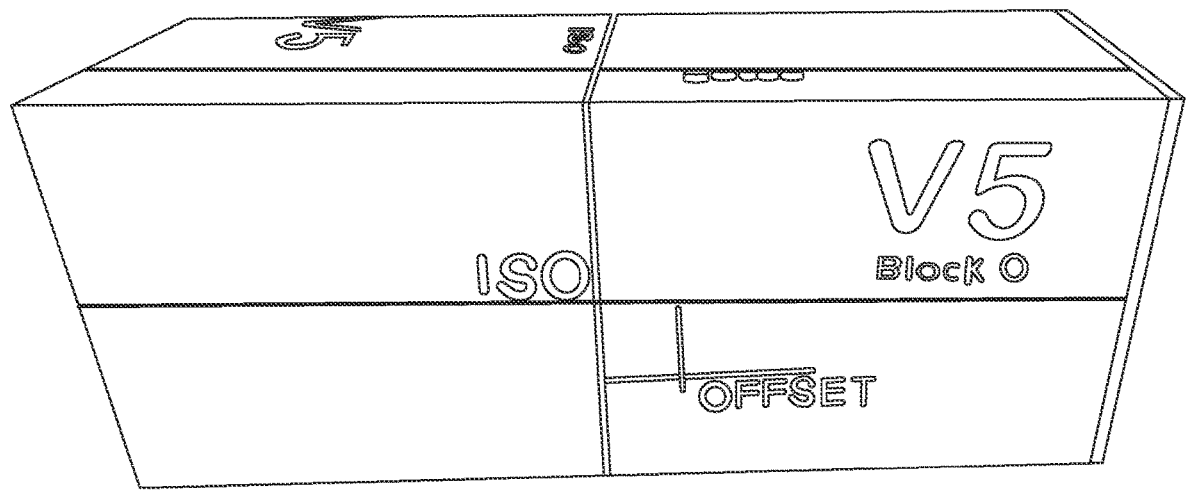
Figure 24:
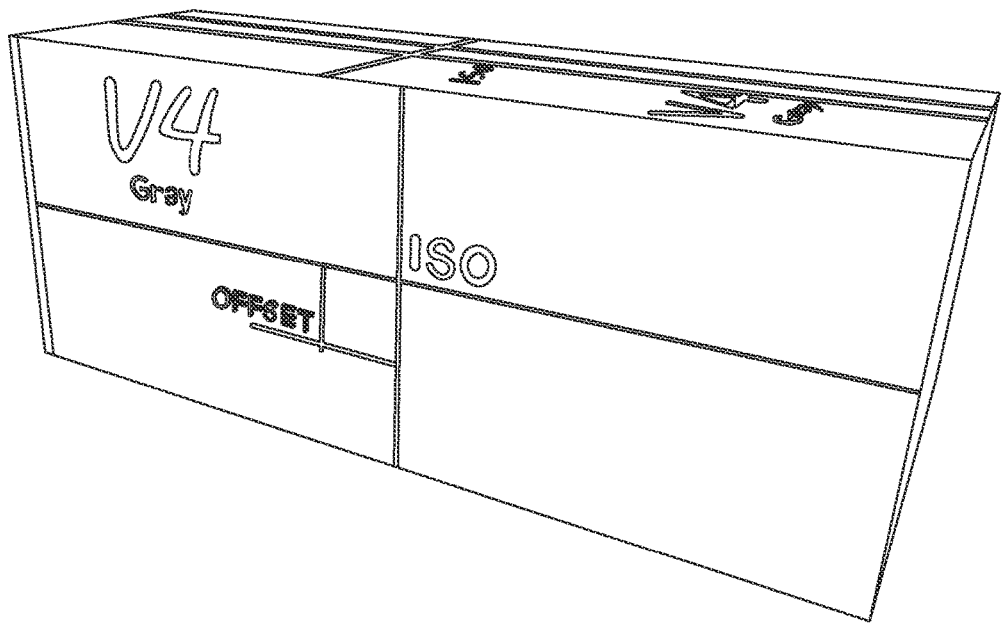
Figure 25:
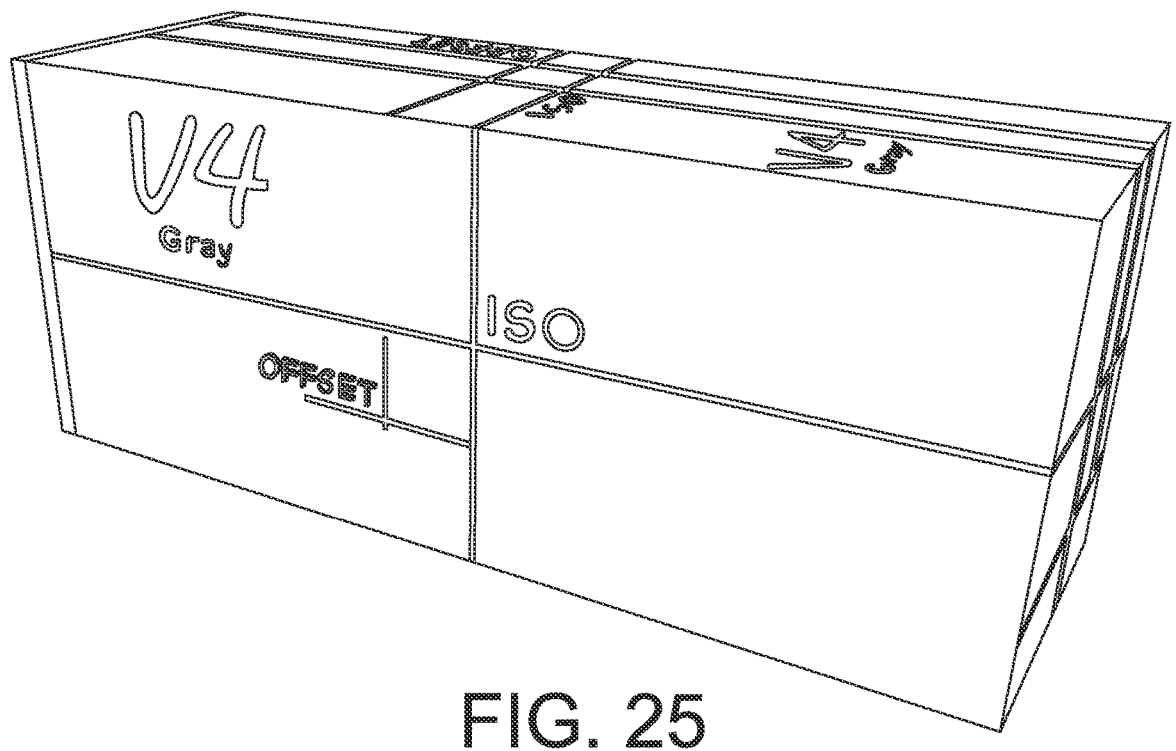
Figure 26:
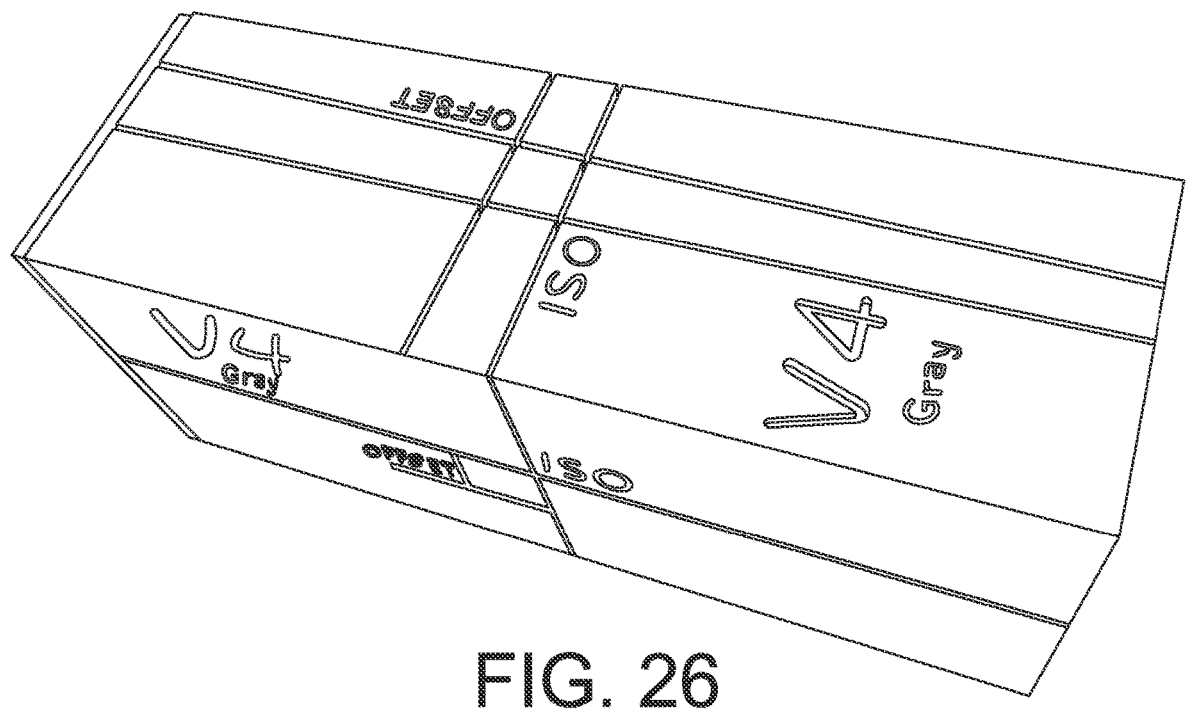
Figure 27:
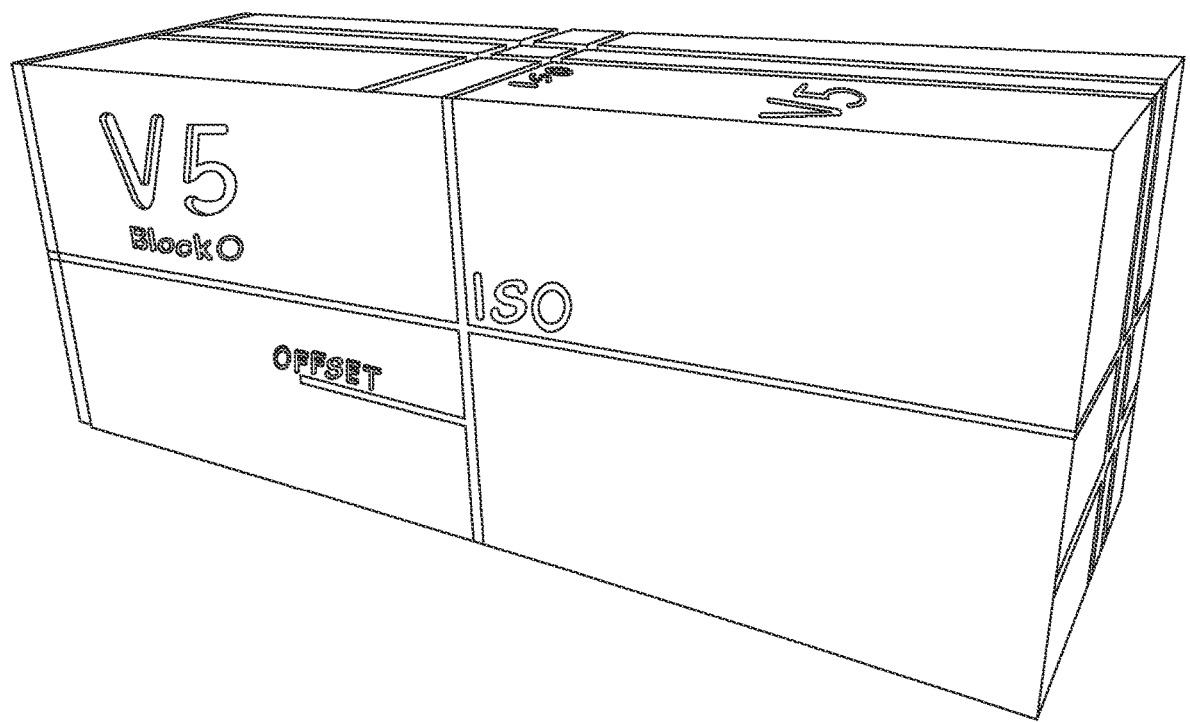
Figure 28:
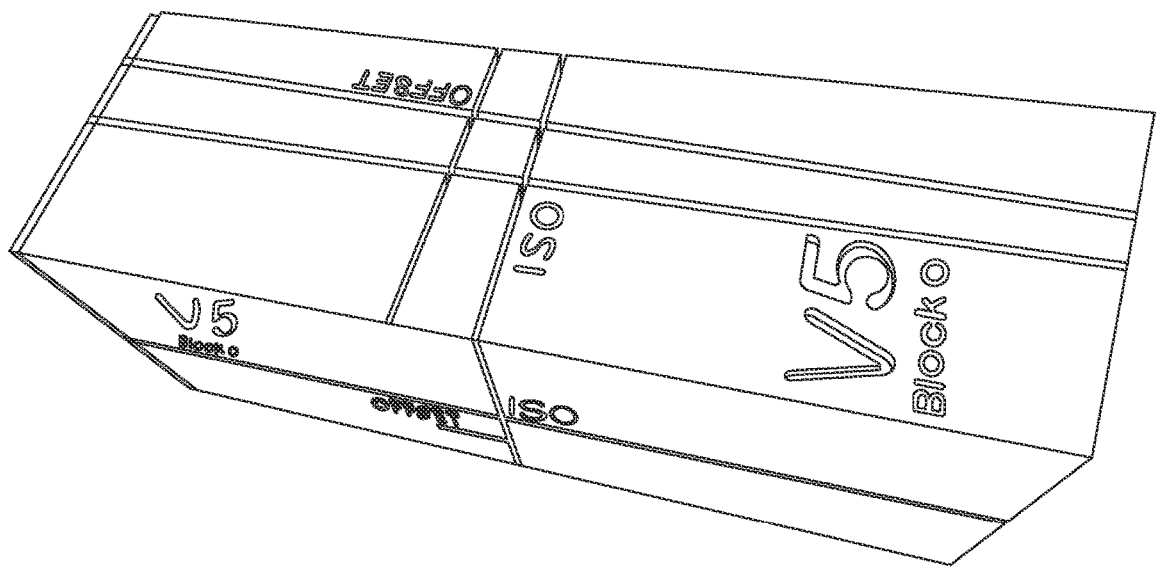
Figure 29:
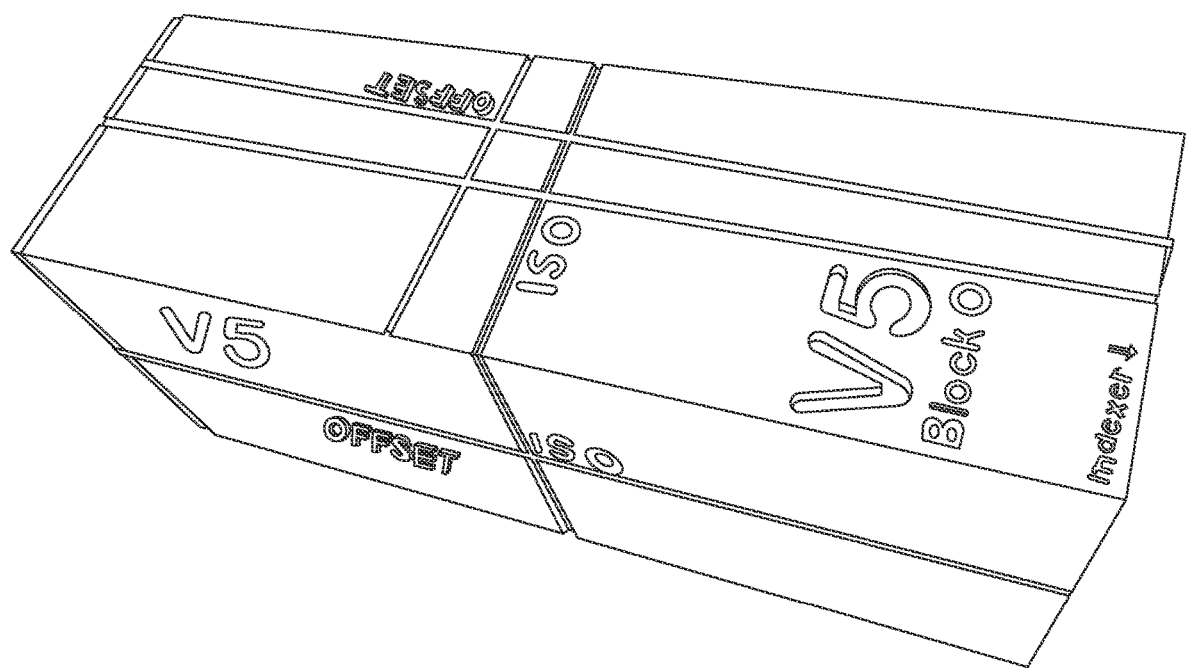
Figure 30:
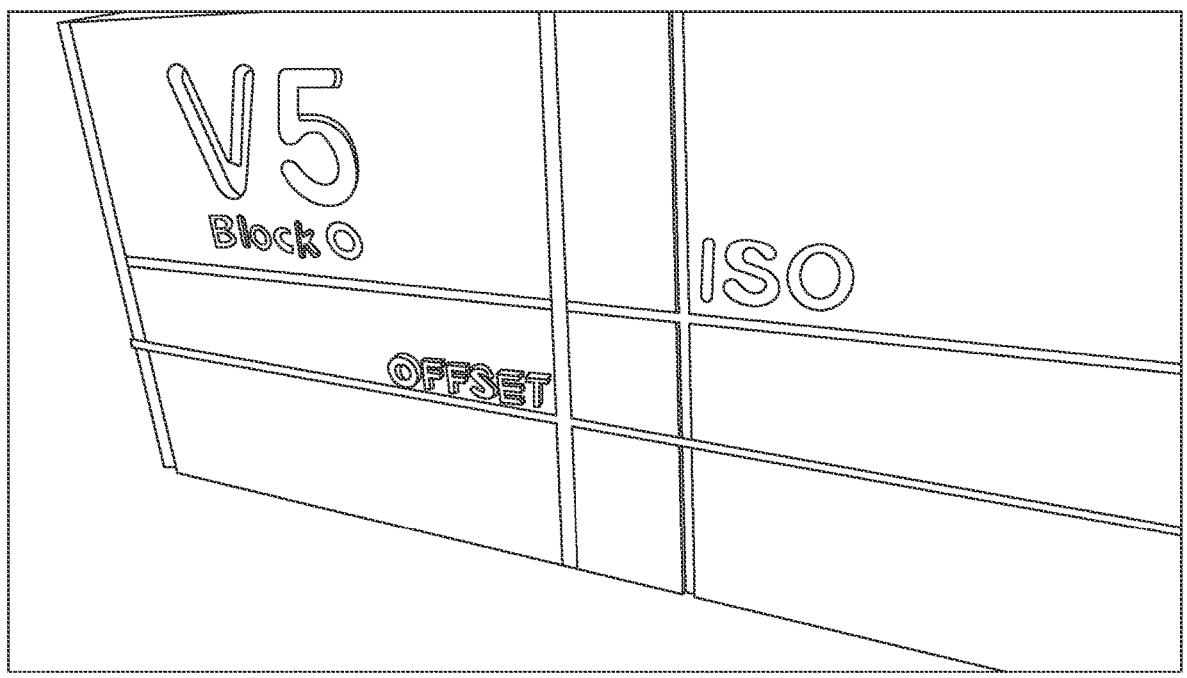
Figure 31:
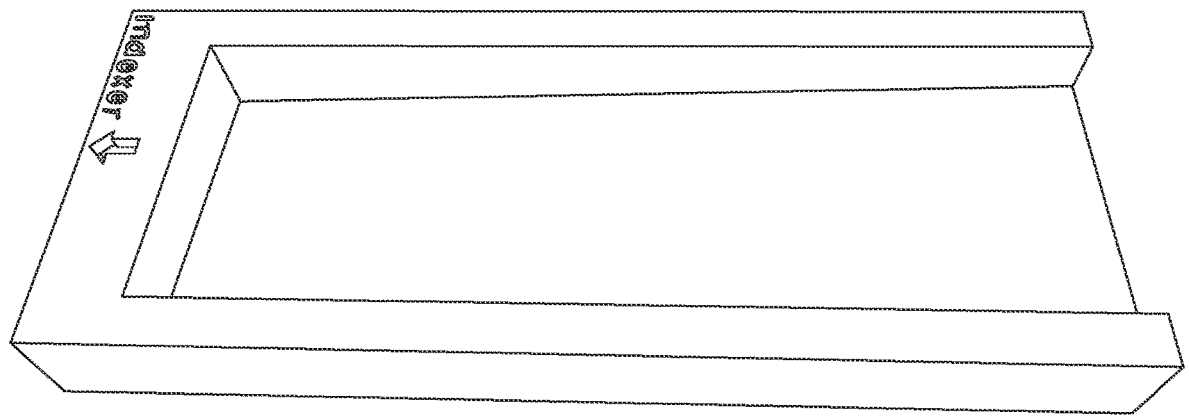
Figure 32:
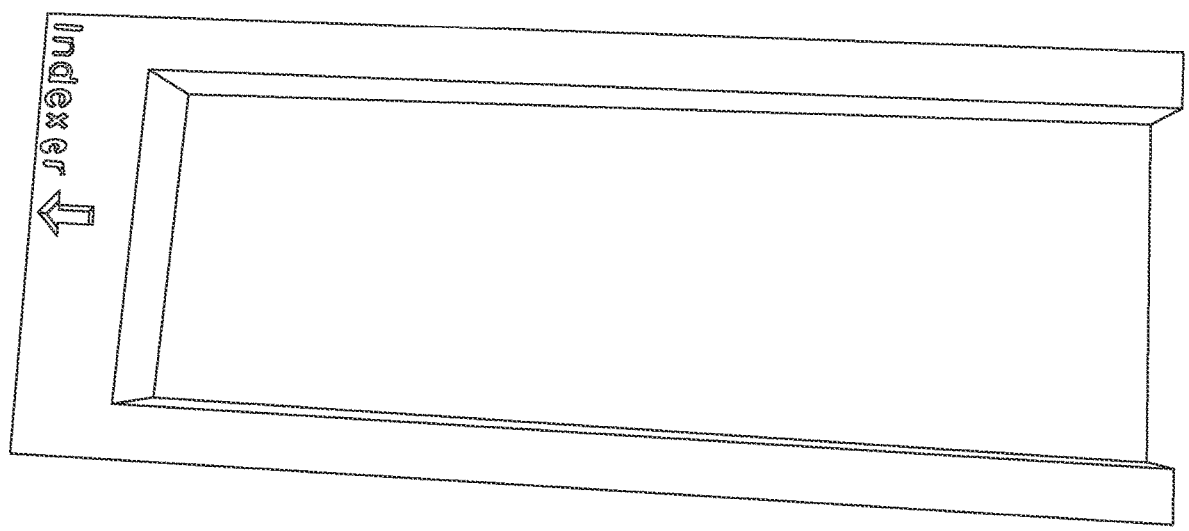
Figure 33:
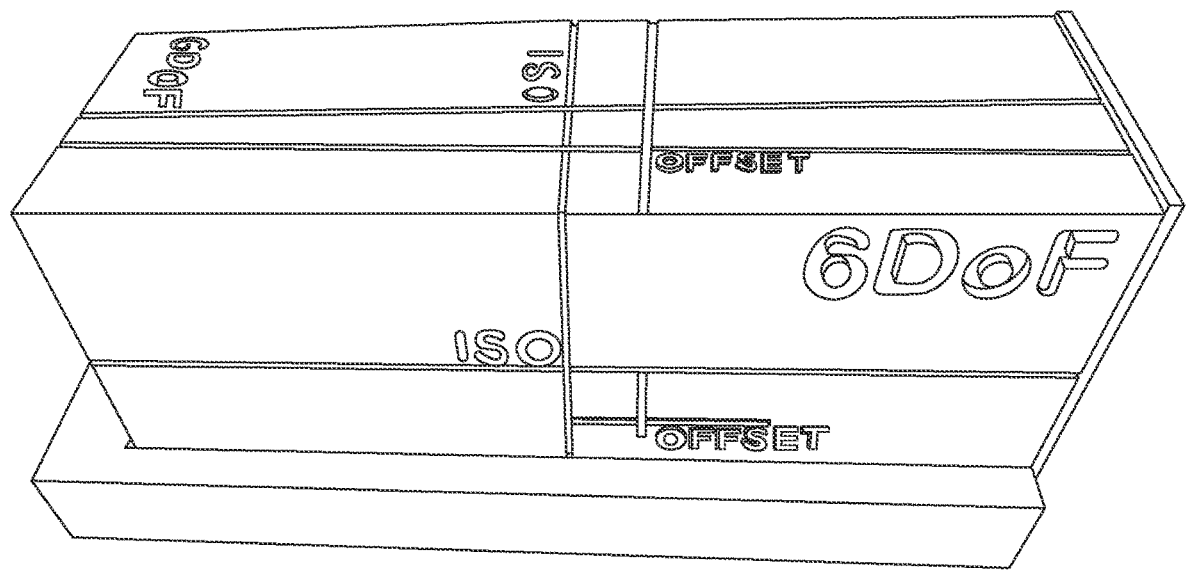
Figure 34:
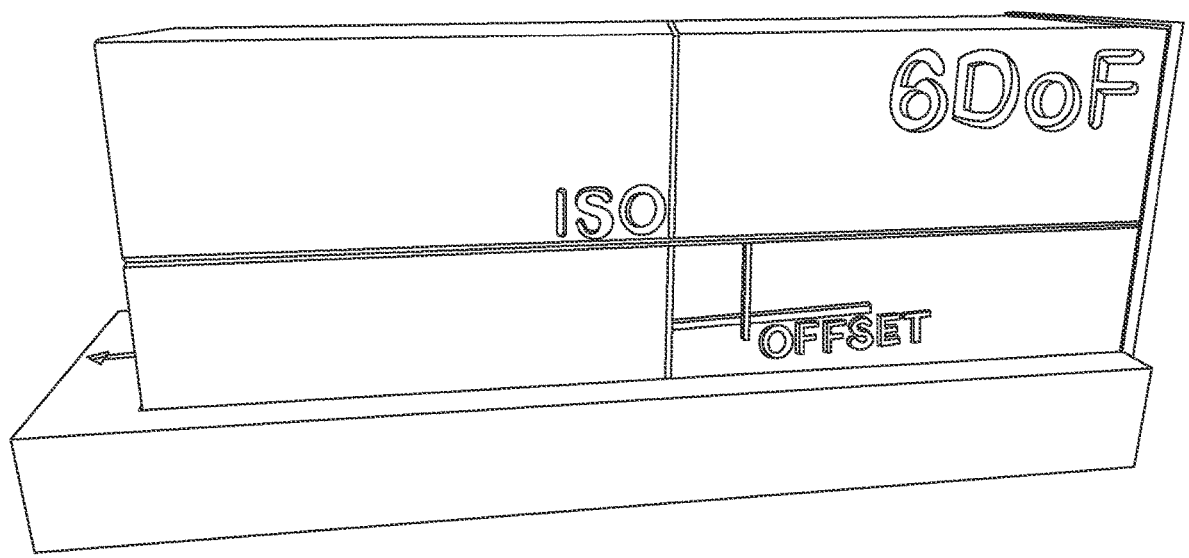
Figure 35:
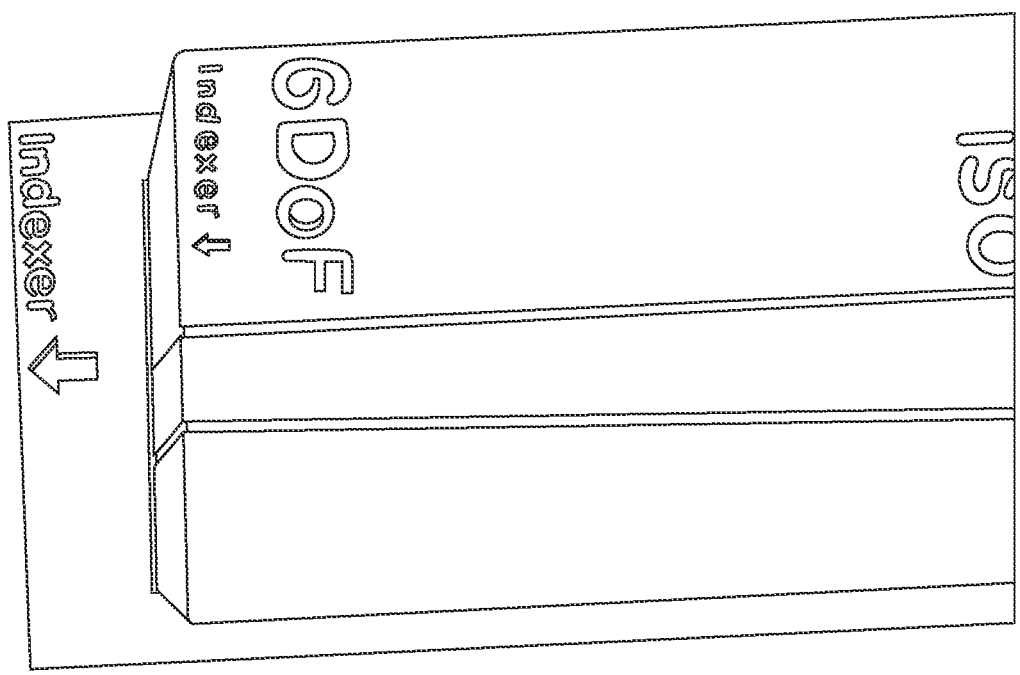

Minimum Δmax, maximum Δmax, average Δmax, and uncertainty within the 95th percentile (2σ) were tabulated. The largest Δmax recorded within the 30 measurements was 0.98 mm for LINAC 1, and the smallest Δmax recorded was 0.49 mm on LINAC 3. The average Δmax values were 0.69 mm, 0.81 mm, and 0.62 mm for LINACs 1, 2, and 3, respectively. The 95% confidence level was within 0.20 mm or smaller for each of the LINACs. FIGS. 17 and 18 show the Δmax data in a linear and box plot style for each exemplary LINAC, respectively. In the FIG. 18 boxplot, the red line represents the median value, the box represents the 68th percentile, the whiskers represent the 95th percentile, and the red '+' are outliers of that respective LINAC's data. Only LINAC 1 and 3 have one outlier outside the 2σ data range. After delivery of the WL test, a visual inspection of the laser and field lights were performed in order to verify that they were impinging on the 1 mm indentations of the phantom. The test was analyzed with either a pass or fail criteria. The laser and light field test passed for each exemplary LINAC for the 30 day period.

Discussion

6DoF robotic tables are a relatively new technology that allows for two additional degrees of rotational freedom compared to a traditional 4DoF table. The additional degrees of freedom have the potential to deliver a more accurate treatment and could allow for a clinician to decrease target margins while sparing more normal tissue.3-5, 7-13 While there have been previous studies that have established the accuracy of various commercial 6DoF tables 4, 5, 14, there has yet to be a streamlined test to efficiently test the quality assurance of the robotic motion of the 6DoF table. In this study, emerging 3D printing technology was utilized in order to fabricate a phantom that could quickly and effectively test 6DoF motion in accordance with TG-142 tolerances.

For a stereotactic LINACs, TG-142 requires table positioning/repositioning to be within 1 mm and 0.5°, mechanical and radiation isocenter coincidence within 1 mm of baseline, and laser localization to be within 1 mm.2 Although TG-142 specifies these tests to be performed at different intervals, this study performed all three on a daily basis based on established institutional policy.

For the registration data that was collected over a 30 day period, each exemplary LINAC's phantom showed minimal uncertainty in both the translational and rotational adjustments. However, when comparing average values to the engineered offsets in the CAD model, the deviation is large enough not to use the CAD values as baseline numbers. For instance, the average values for the lateral and roll adjustments for LINAC 2 were 1.39 cm and 2.6°, respectively. If the designed 1.50 cm and 2.0° values were used as expected values, the positioning/repositioning test would exceed the tolerance of 1.0 mm and 0.5° specified by TG-142. However, within a 95% confidence interval, each individual LINAC's registration uncertainty were below the TG-142 tolerances for both translation and rotation. Notably, the largest variations stemmed from the lateral and yaw adjustments, as there was an uncertainty ranging from 0.7-0.8 mm and 0.2-0.4°, respectively. The most likely cause for this variation could manifest from the inconsistent alignment when abutting the phantom to the indexing bar. Assuming an initial 0.0° rotation in the pitch and roll, the phantom will always be flush to the table given gravitational forces. Hence the small uncertainty observed at 0.1° for both pitch and roll. However, even if the table yaw is 0.0°, it will depend on the user to establish a flush alignment against an index bar, in which even slight yaw rotations from baseline could be corrected during the registration process. With the larger yaw uncertainty, the lateral translation adjustment would also be effected given its travel in the same plane of rotation.

When the registration statistics for each exemplary LINAC are combined (N=90 for all three exemplary LINACs), the uncertainty for each 6DoF adjustment increases such that either each adjustment approaches or even exceeds TG-142 tolerances. Specifically, the 2σ uncertainty values increase to 1.3 mm, 0.9 mm, 1.0 mm, 0.4°, 0.3°, and 0.4° for the vertical, longitudinal, lateral, pitch, roll, and yaw adjustment, respectively. Given this increase, it would be more likely that the periodic QA would fail if these combined values were used as baseline. Therefore, it is recommended that each exemplary LINAC's individual phantom have established baseline registration values rather than using a combined or expected value taken from a CAD model. The modified WL test is similar to the method used by Du et al.[32] Instead of visually aligning the phantom to the mechanical isocenter by either the laser or field lights, the isocenter was carefully defined in the treatment planning system as the center of the BB. Thus, if the online registration shifts were properly performed, the table would move the center of the embedded BB to the treatment isocenter. After delivery of the WL fields, the mechanical isocenter would be visually inspected, as it would be prior to delivery of a traditional WL test. The 1.0 mm lines designed in the phantom represented the center of the BB which would be verified with the laser and field lights. Given this workflow, the WL test now inherently includes more uncertainties throughout the end-to-end process. Uncertainties originating from the reference CT and CBCT spatial positioning, random error in user dependency in localizing treatment isocenter exactly at the BB center in the treatment planning system, uncertainties arising from the registration algorithm, and any variation in table positioning are included in the overall maximum total displacement value used for the WL measurement. However, even with these additional uncertainty considerations, the results from the three exemplary LINACs over a 30 day period were below 1.0 mm. The Δmax range for all three exemplary LINACs ranged from 0.49 to 0.98 mm, with the average falling between 0.62 to 0.81 mm. Linac 2 showed a noticeable increase in average Δmax values. This is most likely machine-specific related, as this particular stereotactic LINAC is two years older than LINAC 1 and 3.

It should be emphasized that the accuracy needed for the tests using the prototype phantom are dependent on the performance of the 3D printer. As of 2014, there are two dozen different varieties of 3D printing processes. Furthermore, the 3D printing 280 market in 2014 was $700 million industry, with an increased projection of $9 billion within ten years from that year.[33] Thus, unlike the QA phantom market in radiation oncology, the options for 3D printers are relatively vaster. When choosing a 3D printer capable of having the same precision as a commercially available phantom, it is important to consider the specifications and additional features. Most importantly, the printer would need to provide sub-millimeter accuracy, as most TG-142 tolerances for stereotactic purposes require less than or equal to 1 mm. While the quoted specifications of the printer stated sub-millimeter accuracy, it was observed that the variance between each phantom and the designed offset dimensions were on the order of millimeter magnitude. This could stem from additional factors beyond specifications from nozzle armature precision. Amid our initial iterations of printing, the phantom would both warp and detach from the printer bed. This can be alleviated by having a printer with a heated bed and proper insulation. Commercial adhesive can also be applied to the bed of the printer in order to affix the first layer of material to the bed surface in order to prevent detachment. Other features like supporting structures, percent infill, and printer speed can also affect the quality of the print. While this is not an exhaustive list of 295 considerations, the user needs to be aware of the capabilities of the 3D printer and gain experience using the printer in order to characterize its printing capacity. By fully understanding the 3D printer, one can fabricate the most optimal QA phantom.

As discussed above, other manufacturing methods could be used to make a phantom according to principles described herein.

FIGS. 19-35 are photographs of various prototypes of a phantom according to principles of the present disclosure.

CONCLUSION

This study investigated the use of a 3D printed phantom in order to perform a streamlined, end-to-end QA test on a 6DoF table. Three individual 3D printed phantoms for three exemplary LINACs were fabricated with known translational and rotational offsets from a central BB. The phantom was CT simulated in a corrected orientation as a reference. A plan was created with a CBCT setup field followed by WL fields for mechanical and radiation isocenter verification using an EPID. The phantom was setup to the designed offset marks, cone-beamed and 6DoF registered, delivered and analyzed the WL fields, and verified proper positioning/repositioning with alignment marks indicating isocenter for 30 days at each exemplary LINAC. Registration uncertainty values were below TG-142 translation and rotation tolerances for each exemplary LINAC. Maximum total displacement values for WL analysis were below 1.0 mm, and laser and light field verification passed for each exemplary LINAC. With an acceptable 3D printer with sub-millimeter accuracy, a QA phantom can be constructed that can efficiently test the robotics of a 6DoF table.

REFERENCES

1. Xing L, Thorndyke B, Schreibmann E, et al. Overview of image-guided radiation therapy. *Med Dosim.* 2006; 31(2): 91-112.

2. Klein E E, Hanley J, Bayouth J, et al. Task Group 142 report: quality assurance of medical accelerators. *Med Phys.* 2009; 36(9):4197-4212.
3. Jin J Y, Yin F F, Tenn S E, Medin P M, Solberg T D. Use of the BrainLAB ExacTrac X-Ray 6D system in image-guided radiotherapy. *Med Dosim.* 2008; 33(2):124-134.
4. Takakura T, Mizowaki T, Nakata M, et al. The geometric accuracy of frameless stereotactic radiosurgery using a 6D robotic couch system. *Phys Med Biol.* 2010; 55(1):1-10.
5. Takemura A, Ueda, S., Noto, K., Kojima, H., Isomura, N. Comparison of the motion accuracy of a six degrees of freedom radiotherapy couch with and without weights. *International Journal of Medical Physics, Clinical Engineering and Radiation Oncology.* 2013; 2:69-75.
6. Ayan A S, Lin H, Yeager C, et al. Should image rotation be addressed during routine cone-beam CT quality assurance? *Phys Med Biol.* 2013; 58(4):1059-1073.
7. Gevaert T, Verellen D, Engels B, et al. Clinical evaluation of a robotic 6-degree of freedom treatment couch for frameless radiosurgery. *Int J Radiat Oncol Biol Phys.* 2012; 83(1):467-474.
8. Dhabaan A, Schreibmann E, Siddiqi A, et al. Six degrees of freedom CBCT-based positioning for intracranial targets treated with frameless stereotactic adiosurgery. *J Appl Clin Med Phys.* 2012; 13(6):3916.
9. Chiesa S, Placidi L, Azario L, et al. Adaptive optimization by 6 DOF robotic couch in prostate volumetric IMRT treatment: rototranslational shift and dosimetric consequences. *J Appl Clin Med Phys.* 2015; 16(5):5525.
10. Shi C, Tazi A, Fang D X, Iannuzzi C. Study of ExacTrac X-ray 6D IGRT setup uncertainty for marker-based prostate IMRT treatment. *J Appl Clin Med Phys.* 2012; 13(3): 3757.
11. Huang C Y, Tehrani J N, Ng J A, Booth J, Keall P. Six degrees-of-freedom prostate and lung tumor motion measurements using kilovoltage intrafraction monitoring. *Int J Radiat Oncol Biol Phys.* 2015; 91(2):368-375.
12. Guckenberger M, Meyer J, Wilbert J, Baier K, Sauer O, Flentje M. Precision of image-guided radiotherapy (IGRT) in six degrees of freedom and limitations in clinical practice. *Strahlenther Onkol.* 2007; 183(6):307-313.
13. Schmidhalter D, Malthaner M, Born E J, et al. Assessment of patient setup errors in IGRT in combination with a six degrees of freedom couch. *Z Med Phys.* 2014; 24(2):112-122.
14. Schmidhalter D, Fix M K, Wyss M, et al. Evaluation of a new six degrees of freedom couch for radiation therapy. *Med Phys.* 2013; 40(11):111710.
15. Dodziuk H. Applications of 3D printing in healthcare. *Kardiochir Torakochirurgia Pol.* 2016; 13(3):283-293.
16. Tack P, Victor J, Gemmel P, Annemans L. 3D-printing techniques in a medical setting: a systematic literature review. *Biomed Eng Online.* 2016; 15(1):115.
17. Brandmeir N J, McInerney J, Zacharia B E. The use of custom 3D printed stereotactic frames for laser interstitial thermal ablation: technical note. *Neurosurg Focus.* 2016; 41(4):E3.
18. Ripley B, Levin D, Kelil T, et al. 3D printing from MRI Data: Harnessing strengths and minimizing weaknesses. *J Magn Reson Imaging.* 2017; 45(3):635-645.
19. Jung J W, Lee J S, Cho D W. Computer-aided multiple-head 3D printing system for printing of heterogeneous organ/tissue constructs. *Sci Rep.* 2016; 6:21685.
20. Canters R A, Lips I M, Wendling M, et al. Clinical implementation of 3D printing in the construction of patient specific bolus for electron beam radiotherapy for non-melanoma skin cancer. *Radiother Oncol.* 2016; 121 (1):148-153.
21. Park K, Park S, Jeon M J, et al. Clinical application of 3D-printed-step-bolus in post-total mastectomy electron conformal therapy. *Oncotarget.* 2016.
22. Su S, Moran K, Robar J L. Design and production of 3D printed bolus for electron radiation therapy. *J Appl Clin Med Phys.* 2014; 15(4):4831.
23. Avelino S R, Silva L F, Miosso C J. Use of 3D-printers to create intensity-modulated radiotherapy compensator blocks. *Conf Proc IEEE Eng Med Biol Soc.* 2012; 2012: 5718-5721.
24. Lee M Y, Han B, Jenkins C, Xing L, Suh T S. A depth-sensing technique on 3D-printed compensator for total body irradiation patient measurement and treatment planning. *Med Phys.* 2016; 43(11):6137.
25. Michiels S, D'Hollander A, Lammens N, et al. Towards 3D printed multifunctional immobilization for proton therapy: Initial materials characterization. *Med Phys.* 2016; 43(10):5392.
26. Cunha J A, Mellis K, Sethi R, et al. Evaluation of PC-ISO for customized, 3D Printed, gynecologic 192-Ir HDR brachytherapy applicators. *J Appl Clin Med Phys.* 2015; 16(1):5168.
27. Ricotti R, Vavassori A, Bazani A, et al. 3D-printed applicators for high dose rate brachytherapy: Dosimetric assessment at different infill percentage. *Phys Med.* 2016; 32(12): 1698-1706.
28. Ehler E D, Barney B M, Higgins P D, Dusenbery K E. Patient specific 3D printed phantom for IMRT quality assurance. *Phys Med Biol.* 2014; 59(19):5763-5773.
29. Madamesila J, McGeachy P, Villarreal Barajas J E, Khan R. Characterizing 3D printing in the fabrication of variable density phantoms for quality assurance of radiotherapy. *Phys Med.* 2016; 32(1):242-247.
30. Bieniosek M F, Lee B J, Levin C S. Technical Note: Characterization of custom 3D printed multimodality imaging phantoms. *Med Phys.* 2015; 42(10):5913-5918.
31. Lutz W, Winston K R, Maleki N. A system for stereotactic radiosurgery with a linear accelerator. *Int J Radiat Oncol Biol Phys.* 1988; 14(2):373-381.
32. Du W, Yang J N, Chang E L, et al. A quality assurance procedure to evaluate cone-beam CT image center congruence with the radiation isocenter of a linear accelerator. *J Appl Clin Med Phys.* 2010; 11(4):3297.
33. Ventola C L. Medical Applications for 3D Printing: Current and Projected Uses. *P T.* 2014; 39(10):704-711.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A three-dimensional phantom for aligning a linear accelerator for radiation therapy equipped with a six degrees-of-freedom (6DoF) treatment table, comprising:
   a body having at a top face, a side face and an end face;
     the top face and the side face sharing a common edge;
     the top face and the end face sharing a common edge; and
     the side face and the end face sharing a common edge;

wherein an angle formed by the top face and the end face is less than 90 degrees;

the side face including a first isocenter mark and a first offset mark, wherein the first offset mark has an angle corresponding to the angle formed by the top face and the end face; and an isocenter marker at the isocenter of the body.

2. The three-dimensional phantom of claim 1, wherein the body comprises a material to simulate human tissue.

3. The three-dimensional phantom of claim 1, further comprising a unique registration mark on at least the side face.

4. The three dimensional phantom of claim 3, wherein the unique registration mark is embossed in the side face of the phantom.

5. The three-dimensional phantom of claim 3, wherein the unique registration mark includes an asymmetrical character.

6. The three-dimensional phantom of claim 1, wherein the first isocenter mark includes a first linear visual mark and a second linear visual mark, the first linear visual mark and the second linear visual mark orthogonal to each other in a first plane.

7. The three-dimensional phantom of claim 1, wherein the first offset mark includes a first linear visual offset mark and a second linear visual offset mark, wherein an angle between the first linear visual offset mark and the second linear visual offset mark in a first plane is 90 degrees.

8. The three-dimensional phantom of claim 1, wherein the first isocenter mark and the second isocenter mark indicate a projected position of the center of a ball bearing.

9. The three-dimensional phantom of claim 1, the end face includes a second isocenter mark and a second offset mark, wherein the second offset mark has an angle corresponding to an angle formed by the top face and the side face.

10. A method of performing an alignment test for a computer tomography (CT) table having 6 degrees of freedom for use with a linear accelerator (LINAC) having alignment lasers, the method comprising:

placing a three-dimensional phantom on the CT table, the three-dimensional phantom having a body having at a top face, a side face and an end face; the top face and the side face sharing a common edge; the top face and the end face sharing a common edge; and the side face and the end face sharing a common edge; wherein an angle formed by the top face and the end face is less than 90 degrees; the side face including a first isocenter mark and a first offset mark, wherein the first offset mark has an angle corresponding to the angle formed by the top face and the end face; and an isocenter marker at the isocenter of the body;

aligning the alignment lasers with the first offset mark;

performing a cone-beam scan of the three-dimensional phantom to produce a data set;

comparing the data set with an initial data set previously generated with respect to the phantom leveled to be a true rectangular prism to produce a displacement profile to correct for translations in at least one of the lateral, longitudinal and vertical directions, roll, pitch and yaw of the CT table; and applying the displacement profile to CT table; and verifying alignment of the CT table by checking alignment of the alignment lasers against the isocenter marks.

11. The method of claim 10, wherein the first isocenter mark includes a first linear visual mark and a second linear visual mark, the first linear visual mark and the second linear visual mark orthogonal to each other in a first plane.

12. The method of claim 10, wherein the displacement profile includes translations for the lateral, longitudinal and vertical directions.

13. The method of claim 10, wherein the displacement profile includes translations for roll, pitch and yaw of the CT table.

14. The method of claim 10, wherein the body comprises a material to simulate human tissue.

15. The method of claim 10, further comprising a unique registration mark on at least the side face.

16. The method of claim 15, wherein the unique registration mark is used for verifying alignment of the phantom on the CT table.

17. The method of claim 10, wherein the unique registration mark is embossed in the side face of the phantom.

18. The method of claim 10, wherein the unique registration mark includes an asymmetrical character.

* * * * *